US012121735B2

(12) United States Patent
Nidelkoff et al.

(10) Patent No.: US 12,121,735 B2
(45) Date of Patent: Oct. 22, 2024

(54) FEEDTHROUGH ASSEMBLY WITH FEATURE FOR CONTROLLING COMPONENT POSITION

(71) Applicant: Medtronic, Inc., Minneapolis, MN (US)

(72) Inventors: Michael J. Nidelkoff, White Bear Lake, MN (US); Lance B. Lohstreter, Brooklyn Park, MN (US); Brad C. Tischendorf, Minneapolis, MN (US); Paul B. Aamodt, Prior Lake, MN (US); Matthew J. Sanders, Wayzata, MN (US)

(73) Assignee: Medtronic, Inc., Minneapolis, MN (US)

( * ) Notice: Subject to any disclaimer, the term of this patent is extended or adjusted under 35 U.S.C. 154(b) by 425 days.

(21) Appl. No.: 17/645,914

(22) Filed: Dec. 23, 2021

(65) Prior Publication Data

US 2022/0118263 A1    Apr. 21, 2022

Related U.S. Application Data

(62) Division of application No. 16/421,008, filed on May 23, 2019, now Pat. No. 11,224,754.

(51) Int. Cl.
*A61N 1/375* (2006.01)
*H05K 5/00* (2006.01)
(Continued)

(52) U.S. Cl.
CPC ......... *A61N 1/3754* (2013.01); *H05K 5/0091* (2013.01); *H05K 5/0247* (2013.01); *C03B 23/00* (2013.01); *Y10T 29/49146* (2015.01)

(58) Field of Classification Search
CPC ............... A61N 1/3754; H01M 50/543; Y10T 29/49002; Y10T 29/49146
(Continued)

(56) References Cited

U.S. PATENT DOCUMENTS 4,841,101 A    6/1989  Pollock
7,725,177 B2   5/2010  Iyer
(Continued)

FOREIGN PATENT DOCUMENTS

DE            10059373 A1    7/2001

OTHER PUBLICATIONS

PCT/US2020/024862, PCT The International Search Report and Written Opinion, mailed Jun. 15, 2020, 10 pages.
(Continued)

*Primary Examiner* — Thiem D Phan
(74) *Attorney, Agent, or Firm* — Shumaker & Sieffert, P.A.

(57) ABSTRACT

In some examples, a feedthrough assembly for a medical device may include a ferrule. The ferrule defines an aperture extending through the ferrule from an outer end surface defined by the ferrule to an end inner end surface defined by the ferrule. The aperture includes a first portion having a first diameter and a second portion having a second diameter less than the first diameter. The aperture defines a longitudinal axis extending therethrough and the ferrule defines a ledge between the first and second portions of the aperture that extends radially inward toward the longitudinal axis. The feedthrough assembly further may include a conductive pin within the aperture and an insulating member surrounding at least a portion of the pin. The insulating member may electrically insulate the conductive pin from the ferrule, and the ledge and a surface of the insulating member adjacent the ledge may define a space therebetween.

9 Claims, 10 Drawing Sheets

(51) Int. Cl.
*H05K 5/02* (2006.01)
*C03B 23/00* (2006.01)

(58) Field of Classification Search
USPC .......................... 29/841, 825, 832, 852, 856
See application file for complete search history.

(56) References Cited

U.S. PATENT DOCUMENTS

| | | |
|---|---|---|
| 8,160,707 B2 | 4/2012 | Iyer et al. |
| 8,288,654 B2 | 10/2012 | Taylor et al. |
| 8,604,341 B2 * | 12/2013 | Barry ........................ H02G 3/02 |
| | | 174/50.56 |
| 9,741,463 B2 | 8/2017 | Leedecke et al. |
| 10,734,139 B2 * | 8/2020 | Giese ................... A61N 1/3754 |
| 11,224,754 B2 | 1/2022 | Nidelkoff et al. |
| 2007/0234540 A1 | 10/2007 | Iyer et al. |
| 2009/0079517 A1 | 3/2009 | Iyer |
| 2009/0079518 A1 | 3/2009 | Iyer |
| 2009/0080140 A1 | 3/2009 | Iyer et al. |
| 2009/0321107 A1 | 12/2009 | Taylor et al. |
| 2010/0202096 A1 | 8/2010 | Iyer |
| 2014/0111904 A1 | 5/2014 | Iyer |
| 2015/0045861 A1 | 2/2015 | Goldman et al. |
| 2015/0045862 A1 | 2/2015 | Goldman et al. |
| 2016/0233656 A1 | 8/2016 | Thom |

OTHER PUBLICATIONS

Prosecution History from U.S. Appl. No. 16/421,008, now issued U.S. Pat. No. 11,224,754, dated Mar. 23, 2021 through Sep. 17, 2021, 49 pp.

* cited by examiner

FEEDTHROUGH ASSEMBLY WITH FEATURE FOR CONTROLLING COMPONENT POSITION

This application is a divisional filing of U.S. patent application Ser. No. 16/421,008, filed 23 May 2019, the entire contents of which is incorporated herein by reference.

TECHNICAL FIELD

This disclosure relates generally to medical devices and, more particularly, to electrical feedthroughs for medical devices.

BACKGROUND

Some types of medical devices, such as cardiac pacemakers or implantable cardiac defibrillator systems, may be used to provide cardiac sensing and therapy for a patient via one or more electrodes. Some medical devices include a feedthrough assembly that that provides an electrical pathway between an interior of a hermetically-sealed housing of the medical device to a point outside the housing. The feedthrough assemblies are generally insulated from the housing. Feedthrough assemblies in such devices may make electrical connections between electrical circuitry within a housing of the medical device and leads, electrodes, or sensors external to the housing of the medical device. Some medical devices including a feedthrough assembly may be configured to be implanted subcutaneously in a chest of the patient or within a chamber of a heart of the patient, as examples. Some medical devices having a pulse generator that is configured to be implanted outside of the heart may be electrically connected to one or more implantable medical electrical leads that include one or more electrodes via a feedthrough assembly.

SUMMARY

In general, this disclosure is directed to feedthrough assemblies for medical devices and to techniques for manufacturing such feedthrough assemblies. Example feedthrough assemblies may include a ferrule that defines an aperture, an insulating member, and a conductive pin. The techniques may include assembling the feedthrough assembly and heating the insulating member such that the insulating member melts and flows into contact with the conductive pin.

As an example, a feedthrough assembly may include a ferrule, a conductive pin, and an insulating member configured to electrically insulate the conductive pin from the ferrule. The ferrule may define an outer end surface, an inner end surface, an aperture extending through the ferrule from the outer end surface to the inner end surface, and a longitudinal axis extending through the aperture from the outer end surface to the inner end surface. The conductive pin and the insulating member may be positioned within the aperture with the insulating member surrounding at least a portion of the conductive pin. The insulating member may be configured to support the conductive pin within the ferrule, such as when the insulating member has been heated and flowed into contact with the conductive pin.

The aperture may include a first portion extending from the outer end surface to a point at least halfway from the outer end surface to the inner end surface and a second portion extending from the inner end surface toward the point at least halfway from the outer end surface to the inner end surface. The first portion of the aperture may have a first diameter and the second portion of the aperture may have a second diameter that is less than the first diameter. The ferrule also may define a ledge between the first portion of the aperture and the second portion of the aperture that extends radially inward toward the longitudinal axis defined by the ferrule.

During a technique for manufacturing the feedthrough assembly, the ledge may support the insulating member within the aperture at least prior to a portion of the technique that includes heating the insulating member. The insulting member may include a material configured to melt and flow when heated, such as glass. By providing support to the insulating member at least prior to heating the insulating member, the ledge may help retain the insulating member within the aperture in a desired position prior to heating, which may help ensure that one or more portions of the insulating member assume a desired position and/or shape as the insulating member re-solidifies after heating.

Although the insulating member may be supported by the ledge at least prior to heating the insulating member, at temperatures sufficient for the insulating member to flow, the insulating member may be configured to wet and lift from the ledge due to surface tension, such that the insulating member at least partially fills the space between the pin and the ferrule when the insulating member re-solifidies. The insulating member reach and, in some cases, exceed a temperature sufficient to flow during heating, and may also remain above a threshold flow temperature during a portion of the time it cools. As the insulating member lifts from the ledge, the ledge and a surface of the insulating member adjacent the ledge may define a space therebetween. The feedthrough assembly may further include an adhesive coated onto the surface of the insulating member adjacent the ledge such that the adhesive fills at least a portion of the space.

In some other examples, a feedthrough assembly configured for attachment to a medical device may include a conductive pin and an insulating member. Such other examples may include a ferrule that does not define a ledge or other feature configured to support the insulating member at least prior to heating the insulating member. Instead, such techniques may utilize a support platform tool separate from the feedthrough assembly during the heating that includes a pedestal within a recess to support the insulating member. Although such a pedestal may provide some support to a portion of the insulating member (e.g., a portion closest to the conductive pin), the pedestal may not reliably control the position and/or shape that the insulating member may assume as it re-solidifies during a method of manufacturing the feedthrough assembly. Thus, techniques for manufacturing such example feedthrough assemblies may result in variations in the shape and/or position of the insulating member relative to the conductive pin (i.e., where the insulating member is "pinned"). Such variations may affect the beam length of the conductive pin (i.e., the length of conductive pin extending above the insulating member toward an outer end surface of the ferrule). Issues associated with variations in the beam length of the conductive pin may occur during implantation of an implantable medical device to which the feedthrough assembly is attached if the beam undergoes applied load conditions of a fixed displacement as opposed to a fixed load. Variations in the beam length of the conductive pin may be associated with undesirable variations in the one or more aspects of the mechanical performance of the conductive pin, such as in the cyclic fatigue of the conductive pin.

Additionally, the use of such pedestals to support an insulating member during manufacturing of a feedthrough assembly may cause defects in and/or contamination of one or more components of the feedthrough assembly. For example, as the insulating member lifts away from the pedestal during a method of manufacturing the feedthrough assembly, the insulating member may break off of the pedestal. Additionally, the conductive pin may bend and/or be pulled out from the insulating member as the insulating member re-solidifies if the position and/or shape of the insulating member is not controlled during manufacturing of the feedthrough assembly.

Moreover, pedestals of such support platforms may be a source of contamination of the insulating member. Such pedestals may be formed of graphite, which may be less likely to stick to a glass insulating member than some other materials. However, graphite pedestals may deposit graphite on the insulating member as the feedthrough assembly is removed from the support platform. Graphite or other foreign materials that may be transferred from a pedestal to an insulating member may cause electrical faults with a corresponding feedthrough assembly. Thus, methods of manufacturing feedthrough assemblies that include the use of such pedestals may result in undesirable variations, manufacturing defects, and/or contamination. Moreover, testing may be needed to detect such variation, defects, and/or contamination in feedthrough assemblies manufactured using such methods, thereby adding time and complexity to the manufacturing process.

Example feedthrough assemblies described herein may include a ferrule defining an aperture and a ledge between first and second portions of the aperture that extends radially inward (e.g., from an inner wall of the ferrule that defines the aperture) toward a longitudinal axis defined by the ferrule and that may support an insulating member within the aperture at least prior to heating of the insulating member. In some examples, the ledge may help ensure that the insulating member assumes a desired shape and/or a desired position relative to the conductive pin after the insulating member re-solidifies, which may reduce variations in mechanical performance of the conductive pin that may occur with variations in the beam length of the conductive pin, such as variations in the cyclic fatigue of the conductive pin. Thus, the ledge may eliminate reliance on graphite pedestals during the manufacturing process, thereby eliminating the need to test for manufacturing defects and/or contamination caused by such pedestals. Moreover, in examples in which an adhesive is coated onto a lower surface of the insulating member, the ledge may enable formation of a better "lock" between the adhesive and one or more components of the feedthrough assembly, relative to other ferrules of other example feedthrough assemblies that do not define a ledge.

In one example, a feedthrough assembly for a medical device comprises a ferrule configured for attachment to the medical device. The ferrule defines an outer end surface and an inner end surface, and an aperture extending through the ferrule from the outer end surface to the inner end surface. The aperture comprises a first portion extending from the outer end surface to a point at least halfway from the outer end surface to the inner end surface, the first portion having a first diameter, and a second portion extending from the inner end surface toward the point at least halfway from the outer end surface to the inner end surface, the second portion having a second diameter that is less than the first diameter. The aperture defines a longitudinal axis extending through the aperture from the outer end surface to the inner end surface, and a ledge between the first portion of the aperture and the second portion of the aperture, the ledge extending radially inward toward the longitudinal axis. The feedthrough assembly further comprises a conductive pin within the aperture, and an insulating member within the aperture and surrounding at least a portion of the conductive pin, wherein the insulating member is configured to electrically insulate the conductive pin from the ferrule, and wherein the ledge and a surface of the insulating member adjacent the ledge define a space therebetween.

In another example, a method of manufacturing a feedthrough assembly for a medical device comprises receiving at least a portion of a ferrule configured for attachment to the medical device within a recess defined by a support platform and dimensioned to receive at least the portion of the ferrule. The ferrule defines an outer end surface and an inner end surface, and an aperture extending through the ferrule from the outer end surface to the inner end surface. The aperture comprises a first portion extending from the outer end surface to a point at least halfway from the outer end surface to the inner end surface, the first portion having a first diameter, and a second portion extending from the inner end surface toward the point at least halfway from the outer end surface to the inner end surface, the second portion having a second diameter that is less than the first diameter. The aperture defines a longitudinal axis extending through the aperture from the outer end surface to the inner end surface, and a ledge between the first portion of the aperture and the second portion of the aperture, the ledge extending radially inward toward the longitudinal axis. The method further comprises receiving a conductive pin within the aperture such that the conductive pin extends through the ferrule, and receiving an insulating member configured to electrically insulate the conductive pin from the ferrule within the aperture and around the conductive pin such that at least a portion of the insulating member is positioned between the ledge and the outer end surface of the ferrule. The method further comprises heating the insulating member such that the insulating member melts and flows into contact with the conductive pin, and discontinuing heating of the insulating member and allowing the insulating member to re-solidify. The insulating member is configured lift from the ledge such that the ledge and a surface of the insulating member adjacent the ledge define a space therebetween.

In another example, an implantable medical device comprises a housing, a plurality of electrodes, and circuitry within the housing, the circuitry configured to at least one of sense electrical signals or deliver electrical therapy via the electrodes. The implantable medical device further comprises a feedthrough assembly comprising a ferrule configured for attachment to the medical device. The ferrule defines an outer end surface and an inner end surface, and an aperture extending through the ferrule from the outer end surface to the inner end surface. The aperture comprises a first portion extending from the outer end surface to a point at least halfway from the outer end surface to the inner end surface, the first portion having a first diameter, and a second portion extending from the inner end surface toward the point at least halfway from the outer end surface to the inner end surface, the second portion having a second diameter that is less than the first diameter. The aperture defines a longitudinal axis extending through the aperture from the outer end surface to the inner end surface, and a ledge between the first portion of the aperture and the second portion of the aperture, the ledge extending radially inward toward the longitudinal axis. The feedthrough assembly further comprises a conductive pin within the aperture, and an insulating member within the aperture and surrounding at least a portion of the conductive pin, wherein the insulating member is configured to electrically insulate the conductive pin from the ferrule, and wherein the ledge and a surface of the insulating member adjacent the ledge define a space therebetween.

In another example, a feedthrough assembly comprises a ferrule defining an outer end surface and an inner end surface, and an aperture extending through the ferrule from the outer end surface to the inner end surface. The aperture comprises a first portion extending from the outer end surface to a point at least halfway from the outer end surface to the inner end surface, the first portion having a first diameter, and a second portion extending from the inner end surface toward the point at least halfway from the outer end surface to the inner end surface, the second portion having a second diameter that is less than the first diameter. The aperture defines a longitudinal axis extending through the aperture from the outer end surface to the inner end surface, and a ledge between the first portion of the aperture and the second portion of the aperture, the ledge extending radially inward toward the longitudinal axis. The feedthrough assembly further comprises conductive pin within the aperture, and an insulating member within the aperture and surrounding at least a portion of the conductive pin, wherein the insulating member is configured to electrically insulate the conductive pin from the ferrule, and wherein the ledge and a surface of the insulating member adjacent the ledge define a space therebetween.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
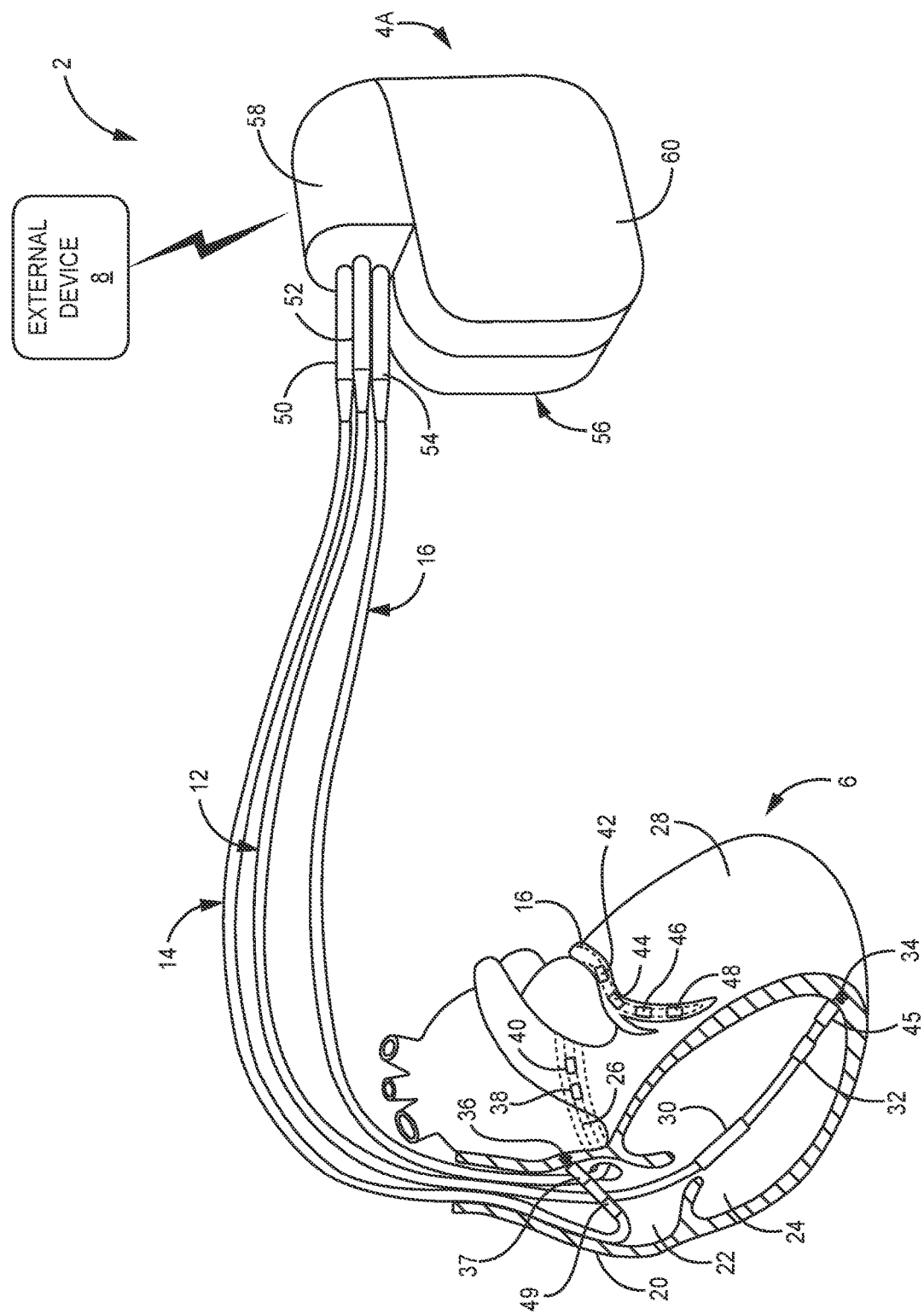
FIG. 1 is a conceptual drawing illustrating an example of a medical device system including an implantable medical device that includes an example feedthrough assembly, and an external device, in conjunction with a patient's heart.

In general, this disclosure describes example feedthrough assemblies for medical devices. Such feedthrough assemblies may include a ferrule, a conductive pin, and an insulating member configured to electrically insulate the conductive pin from the ferrule. In some examples, a feedthrough assembly may include a header structure configured for attachment to a medical device. The header structure may include a ferrule defining one or more apertures, each aperture of which may be associated with a corresponding electrical connection between different components of a medical device. Although the example feedthrough assemblies are generally described herein as being configured for attachment to a medical device, it should be understood that any of the example feedthrough assemblies described herein alternatively may be configured for attachment to a non-medical device.

The ferrule may define an outer end surface, an inner end surface, at least one aperture, and a longitudinal axis extending through the aperture from the outer end surface to the inner end surface. In some examples, the aperture may define a first portion having a first diameter and extending from the outer end surface to a point at least halfway from the outer end surface to the inner end surface. The aperture also may define a second portion that extends from the inner end surface toward the point at least halfway from the outer end surface to the inner end surface and that has a second diameter that is less than the first diameter. In any such examples, the conductive pin and the insulating member of the feedthrough assembly may be positioned within the aperture such that the insulating member surrounds at least a portion of the conductive pin.

In some examples, the ferrule further may define a ledge between the first portion of the aperture and the second portion of the aperture that extends radially inward toward the longitudinal axis defined by the ferrule. For example, the ledge may define a surface in a plane substantially orthogonal to the longitudinal axis. In other examples, the ledge may define a third portion of the aperture that extends between the first portion and the second portion such that a diameter of the third portion tapers from the first diameter at a junction of the third portion and the first portion to the second diameter at a junction of the third portion and the second portion. In still other examples, the ferrule may define an aperture that tapers in diameter from an upper diameter at the outer end surface of the ferrule to a lower diameter at the inner end surface of the ferrule.

In some examples, the insulating member may comprise a material that is configured to melt and flow when heated, such as during a method of manufacturing the feedthrough assembly. In such examples, a ledge defined by the ferrule may be configured to support the insulating structure at least prior to its reaching a temperature at which it may melt and flow, which may help ensure that the insulating member assumes a desired shape and/or position after the insulating member re-solidifies. For example, the ledge may help ensure that the conductive pin has a desired beam length in the finished feedthrough assembly. As the beam length of the conductive pin may have an effect on the mechanical performance of the feedthrough assembly (e.g., from effects of variations in the cyclic fatigue of the conductive pin), controlling the beam length of the conductive pin may help ensure consistent mechanical performance of the feedthrough assembly between different feedthrough assemblies of the same type. In this manner, the example ledges described herein may help ensure desirable mechanical performance of the example feedthrough assemblies described herein. Moreover, such ledges may reduce or eliminate reliance on support pedestals (e.g., a graphite pedestals) of support platforms used during methods of manufacturing such feedthrough assemblies.

In examples in which the ferrule defines a ledge, the ledge and a surface of the insulating member that is adjacent to the ledge may define a space therebetween. The insulating member may be a glass insulating member, which may be configured to melt and flow into contact with the conductive pin during a method of manufacturing the feedthrough assembly. In some such examples, the insulating member may be configured to support the conductive pin within the ferrule at least after the insulating member re-solidifies. In this manner, the insulating member may provide mechanical integrity to the feedthrough assembly in addition to electrically insulating the conductive pin from the ferrule.

In some examples in which a ferrule defines a ledge, the insulating member may be configured to lift from the ledge while flowable and then re-solidify during a method of manufacturing the feedthrough assembly to form a space between the ledge and the surface of the insulating member that is adjacent to the ledge (e.g., a lower surface of the insulating member). In some examples, the feedthrough assembly may further include an adhesive coated onto the surface of the insulating member adjacent the ledge such that the adhesive fills at least a portion of the space. In such examples, the ledge may define additional surface area of the ferrule to which the adhesive may adhere, relative to ferrules of other example feedthrough assemblies that do not define such a ledge. Moreover, a position of the surface of the ledge relative to a surface of the ferrule that defines a second portion of the aperture may help create a "lock" between the adhesive and one or more of the insulating member, the conductive pin, or the ledge. In this manner, the ledge may help improve adhesion between components of the feedthrough assembly and contribute to the mechanical integrity of the feedthrough assembly.

Figure 2:
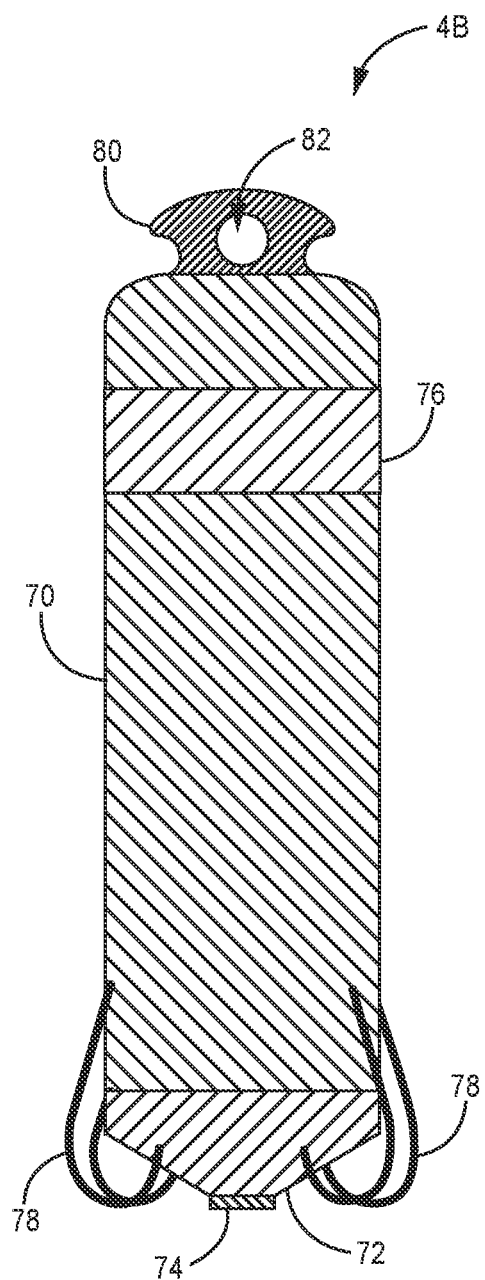
FIG. 2 is a conceptual drawing illustrating an example of a leadless implantable medical device that includes another example feedthrough assembly.

FIGS. 1 and 2 illustrate example medical devices that may include one or more of the example feedthrough assemblies described herein. The example feedthrough assemblies included in the medical devices of FIGS. 1 and 2 may be configured to electrically connect a pulse generator to one or more electrodes. Electrodes of the medical devices of FIGS. 1 and 2 may be configured to deliver an electrical signal (e.g., therapy such as cardiac pacing) and/or configured to provide at least one sensing vector, in accordance with the examples described herein. It should be noted that medical devices that include one or more of the example feedthrough assemblies described herein may not be limited to treatment of a human patient. In alternative examples, medical devices that include one or more of the example feedthrough assemblies described herein may be implemented in non-human patients, e.g., primates, canines, equines, pigs, ovines, bovines, and felines. These other animals may undergo clinical or research therapies that may benefit from the subject matter of this disclosure.

FIG. 1 is a conceptual drawing illustrating an example of medical device system 2, including a leaded IMD 4A and an external device 8, in conjunction with heart 6 of a patient. Medical device system 2, which includes IMD 4A and external device 8, is an example of a medical device system configured to deliver cardiac therapy to heart 6 of the patient. In some examples, IMD 4A may be an implanted, multi-channel cardiac pacemaker, implantable cardioverter-defibrillator (ICD), implantable pulse generator (IPG), extravascular pacemaker and/or ICD, or other IMD or combination of such IMDs configured to deliver cardiac therapy to heart 6. However, some of the components of the IMDs described herein, such as components of a feedthrough assembly, may be utilized with types of external medical devices or other types of IMDs, such as other IMDs configured to deliver cardiac electrical therapy. Although system 2 is described herein in the context of cardiac electrical therapy, one or more aspects of system 2 (e.g., a configuration of a feedthrough assembly of IMD 4A) may be adapted to IMDs configured to deliver other types of electrical therapy to a patient, as well as to IMDs that provide physiological sensing and monitoring, but do not necessarily provide therapy.

In some examples, IMD 4A may be configured to sense electrical signals corresponding to the depolarization and repolarization of heart 6, e.g., a cardiac electrogram (EGM), via electrodes on one or more leads 12, 14, and 16 or the housing of IMD 4A. Additionally, or alternatively, IMD 4A may sense electrical signals corresponding to the depolarization and repolarization of heart 6 via extravascular electrodes (e.g., electrodes positioned outside the vasculature of the patient), such as epicardial electrodes, external surface electrodes, subcutaneous electrodes, and the like. In any such examples, the configurations of electrodes used by IMD 4A for sensing and pacing may be unipolar or bipolar. In some examples, system 2 may determine heart rate to, e.g., detect arrhythmia, based on the electrical signals sensed via the electrodes. IMD 4A may also deliver therapy in the form of electrical signals to heart 6 via electrodes located on one or more leads 12, 14, and 16 or a housing of IMD 4A. In the illustrated example, IMD 4A is connected to leads 12, 14 and 16, and may be communicatively coupled to external device 8.

Leads 12, 14, and 16 extend into heart 6 of the patient to sense electrical activity of heart 6 and to deliver electrical stimulation to heart 6. In the example shown in FIG. 1, RV lead 12 extends through one or more veins (not shown), vena cava 20, RA 22, and into RV 24 for sensing right ventricular cardiac signals and delivering pacing or shocking pulses to RV 24. Right atrial lead 14 extends through one or more veins and vena cava 20 and is positioned such that a distal end of LV lead 16 is in the vicinity of RA 22 and vena cava 20 for sensing right atrial cardiac signals and delivering pacing or shocking pulses to RA 22. LV lead 16 extends through one or more veins, vena cava 20, RA 22, and into coronary sinus 26 (illustrated in phantom) to a region adjacent to the free wall of LV 28 of heart 6. In some examples, electrodes of lead 16 may be used in combination with electrodes of lead 12 and/or lead 14 for delivering electrical shocks for cardioversion and defibrillation therapies. In other examples, lead 16 may also be equipped with a distal tip electrode and ring electrode for pacing and sensing functions in the left chambers of heart 6.

In the illustrated example, lead 12 includes bipolar electrodes 32 and 34, which may be located adjacent to a distal end of lead 12. Lead 14 includes bipolar electrodes 36 and 37, which may be located adjacent to a distal end of lead 14. Lead 16 may be a multipolar LV lead and may include electrodes 38 and 40, and electrodes 42, 44, 46, and 48. In some examples, electrodes 42, 44, 46, and 48 may be located adjacent to a distal end of lead 16, as illustrated in FIG. 1. In some examples, electrodes 38, 40, 42, 44, 46, and/or 48 of lead 16 may be segmented electrodes having a plurality of discrete electrodes arranged at respective circumferential positions around the circumference of lead 16.

Electrodes 34 and/or 36 may be extendable helix tip electrodes and may be mounted retractably within respective insulative electrode heads. For example, electrode 34 may be mounted retractably within insulative electrode head 45 positioned on lead 12 and electrode 36 may be mounted retractably within an insulative electrode head positioned on lead 14 (not shown), respectively. In some examples, one or both of leads 12 and 14 may also include one or more elongated coil electrodes, such as coil electrode 30 of lead 12 and/or a coil electrode 49 of lead 14. In some examples, electrodes 30-49 of leads 12, 14, and 16 may be electrically coupled to a respective conductor within a lead body of a corresponding one of leads 12, 14, and 16, and thereby coupled to circuitry within IMD 4A.

In some examples, leads 12, 14, and 16 respectively include in-line connectors 50, 52, and 54. IMD 4A may further include an IPG 56, which may include a connector block 58 and a hermetically-sealed housing 60. Connector block 58 may house a feedthrough assembly (not shown) configured to electrically connect leads 12, 14, and 16 with electronic components included within housing 60 of IPG 56 via in-line connectors 50, 52, and 54. In-line connectors 50, 52, and 54 may be configured to fit into corresponding bores of connector block 58, which may be coupled to corresponding conductive components of a feedthrough assembly of IPG 56 (e.g., conductive pins), thereby connecting electrodes 30-49 of leads 12, 14, and 16 to IPG 56. The feedthrough assembly of IPG 56 may include a different ferrule for each electrode on leads 12, 14, and 16, each of which may define an aperture in which a conductive pin and an insulating member are received. Each of the conductive pins of the feedthrough assembly may be part of a different corresponding electrical connection between IPG 56 and one of the electrical conductors of leads 12, 14, and 16 via in-line connectors 50, 52, and 54. In some examples, the feedthrough assembly of IPG 56 may include one or more features of the example feedthrough assemblies illustrated in FIGS. 4-9, which may confer one or more advantages described below with respect to such features of the example feedthrough assemblies of FIGS. 4-9.

In some examples, one or more outward-facing portions of housing 60 may be uninsulated, and thus may enable housing 60 to be used as a housing electrode. In some examples, substantially all of housing 60 may be uninsulated, such that substantially all of housing 60 defines the housing electrode. In some other examples, housing 60 may define one or more additional housing electrodes (not shown), which may be defined by corresponding divisions between insulated and uninsulated portions of housing 60.

In some examples, IMD 4A may be configured for sensing of electrical signals corresponding to a cardiac electrogram of heart 6 via any combination of electrodes 30-49 or via any one of electrodes 30-49 in combination with a housing electrode of housing 60. In any such examples, IMD 4A may be configured to deliver cardiac therapy to heart 6 via any combination of electrodes 30-49. For example, IMD 4A may be configured to deliver at least one of fusion pacing or biventricular pacing to heart 6.

The configuration of medical device system 2 illustrated in FIG. 1 is one example configuration and is not intended to be limiting. As discussed in further detail below with respect to FIG. 2, housing 60 may enclose one or more accelerometers, therapy delivery circuitry, which may be configured to generate therapeutic stimulation, such as cardiac pacing, cardioversion, and defibrillation pulses, and sensing circuitry configured to sense electrical signals corresponding to a cardiac electrogram signal of the patient and/or an activity level or activity of the patient. Housing 60 also may enclose and one or more of a memory for storing default and/or allowable values of one or more therapy parameters, diagnostics, feedback from the patient, and/or therapy programs that may include values of one or more cardiac therapy parameters. Housing 60 further may enclose communication circuitry configured for communication between IMD 4A and external device 8 and/or other devices, such as an external device located with a clinician or a server. Such components may enable IMD 4A to transmit data, such as data pertaining to a physiological condition of the patient and/or one or more recommended values of one or more cardiac therapy parameters to external device 8.

FIG. 2 is a conceptual drawing illustrating an example configuration of a leadless IMD 4B. As illustrated in FIG. 2, IMD 4B may include a housing 70 and a cap 72. IMD 4B may be hermetically sealed to enclose and protect electrical components (e.g., processing circuitry, sensing circuitry, therapy delivery circuitry, or other components) within IMD 4B. In some examples, housing 70 and cap 72 may enclose some or all of the electrical components of IMD 4B. All or portions of housing 70 and/or cap 72 may be electrically insulating.

In some examples, IMD 4B may include one or more electrodes, which may be configured to deliver an electrical signal (e.g., therapy such as cardiac pacing) and/or configured to provide at least one sensing vector. For example, IMD 4B may include electrode 74, which may be carried on cap 72, and/or electrode 76, which may be a ring or cylindrical electrode carried on or formed by housing 70 of IMD 4B. As illustrated in FIG. 2, electrode 76 may be disposed on an exterior surface of housing 70 and may be positioned to contact cardiac tissue upon implantation. In some examples, electrode 76 comprises more than one electrode 76. In such examples, one electrode 76 may be used as a cathode and another electrode may be used as an anode for delivering cardiac pacing, such as bradycardia pacing, CRT, ATP, or post-shock pacing. In addition, one or more electrodes 76 may be used to detect intrinsic electrical signals from heart 6, such as an electrocardiogram signal that processing circuitry enclosed within IMD 4B may receive via sensing circuitry enclosed within IMD 4B.

IMD 4B may include a feedthrough assembly (not shown) configured to electrically connect electrode 74 with electronic components included within housing 70 of IMD 4B. For example, a conductive pin of the feedthrough assembly of IMD 4B may include a conductive pin that electrically connects electrode 74 to therapy delivery circuitry within housing 70 of IMD 4B. The feedthrough assembly of IMD 4B may include a single ferrule, a single conductive pin, and a single insulating member. In some examples, the feedthrough assembly of IMD 4B may include one or more features of the example feedthrough assemblies illustrated in FIGS. 4-9, which may confer one or more advantages described below with respect to such features of the example feedthrough assemblies of FIGS. 4-9.

In some examples, a distal end of IMD 4B may include fixation mechanisms 78, which may be configured to attach IMD 4B to patient tissue (e.g., cardiac tissue) and retain electrode 74 in contact with cardiac tissue. Fixation mechanisms 78 may be active fixation tines, screws, clamps, adhesive members, or any other mechanisms for attaching a device to tissue. In some examples, fixation mechanisms 78 may be constructed of a memory material, such as a shape memory alloy (e.g., nickel titanium), that retains a preformed shape. During implantation, fixation mechanisms 78 may be flexed forward to engage tissue and allowed to flex back towards housing 70, thereby embedding fixation mechanisms 78 in patient tissue.

IMD 4B also may include a manipulator attachment feature 80, which may be positioned at a proximal end of IMD 4B. In some examples, manipulator attachment feature 80 may be integral with housing 70. In other examples, manipulator attachment feature 80 may be a separate component of IMD 4B that is attached to housing 70. In any such examples, manipulator attachment feature 80 may have a configuration that defines an opening 82, a hook shape, or any other suitable configuration that may enable tethering or extraction of IMD 4B to or from patient tissue. For example, manipulator attachment feature 80 may be configured to receive or otherwise attach to a manipulator tool configured to enable a clinician to manipulate IMD 4B, such as during a procedure to implant or explant IMD 4B. In some examples, manipulator attachment feature may be configured to attach IMD 4B to patient tissue. For example, a suture or other device may be inserted around and/or through manipulator attachment feature 80 and attached to tissue. In this manner, manipulator attachment feature 80 may provide an attachment structure to tether or retain IMD 4B within patient tissue at an implant site of IMD 4B. Manipulator attachment feature 80 also may be used to extract IMD 4B if IMD 4B is to be explanted (i.e., removed) from patient 4 if such action is deemed desirable.

In some examples, IMD 4B may include one or more leads or electrode-bearing extensions configured to place one or more additional electrodes at another location within the patient, such as another location within a same chamber or a different chamber than a chamber of the patient's heart in which housing 70 may be implanted. In some such examples, housing 70 and cap 72 may carry fewer than all of the electrodes used to perform functions described herein with respect to IMD 4B. In other examples, each electrode of IMD 4B may be carried by one or more leads (e.g., the housing of IMD 4B may not carry any of the electrodes). In still other examples, IMD 4B or another pacing device used with one or more other devices, such as external device 8 of system 2 of FIG. 1.

Figure 3:
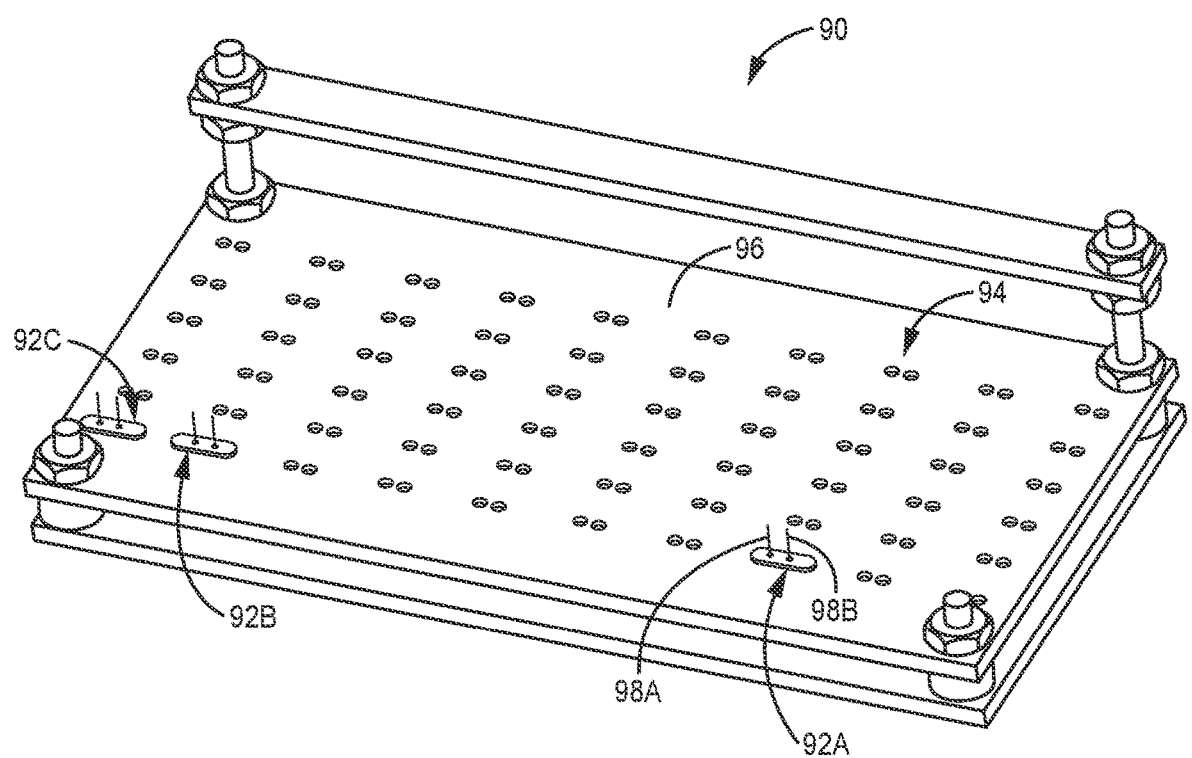
FIG. 3 is a conceptual drawing illustrating a manufacturing device with example feedthrough assemblies received within corresponding recesses defined by a support platform of the manufacturing device.

FIG. 3 is a conceptual drawing of a manufacturing device 90 with example feedthrough assemblies 92A-92C (collectively, "feedthrough assemblies 92") received within corresponding recesses 94 defined by a support platform 96 of the manufacturing device 90. In the example of FIG. 3, manufacturing device 90 is configured for the manufacture of feedthrough assemblies that each include two conductive pins, such as conductive pins 98A and 98B of feedthrough assembly 92A.

Support platform 96 defines recesses 94 in 60 groups of two, in which each group of two recesses 94 is spaced to receive the two conductive pins of a corresponding feedthrough assembly. Thus, in the example of FIG. 3, support platform 96 is configured to hold up to sixty such feedthrough assemblies during one iteration of a method of manufacturing the feedthrough assemblies. In other examples, however, manufacturing device 90 may be configured to hold more than sixty or fewer than sixty feedthrough assemblies that each include two conductive pins. Additionally, or alternatively, support platform 96 may define recesses 94 in other configurations, such as singly or in groups of more than two. In any such examples, manufacturing device 90 may be configured for use in the manufacture of feedthrough assemblies having any suitable number of conductive pins in any suitable arrangement.

Manufacturing device 90 may be formed of any suitable material capable of withstanding temperatures at least as high as those needed to melt an insulating member of a feedthrough assembly without melting or otherwise deforming. For example, one or more portions of manufacturing device 90 may be formed of graphite or another material that would not stick to the feedthrough assemblies 92, e.g., depending on the material(s) of the feedthrough assemblies. In any such examples, manufacturing device 90 does not include support pedestals positioned within recesses 94. For example, manufacturing device 90 does not include graphite pedestals that may deposit graphite residue on insulating members of feedthrough assemblies 92. Instead, one or more internal components of feedthrough assemblies 92 may be configured to provide support to insulating members of feedthrough assemblies 92 during methods of manufacturing feedthrough assemblies 92 that include using manufacturing device 90. In this manner, manufacturing device 90 may reduce or eliminate some of the drawbacks associated with manufacturing devices that include such support pedestals, such as by reducing or preventing contact between graphite of support platform 96 and insulating members of feedthrough assemblies 92.

Figure 6:
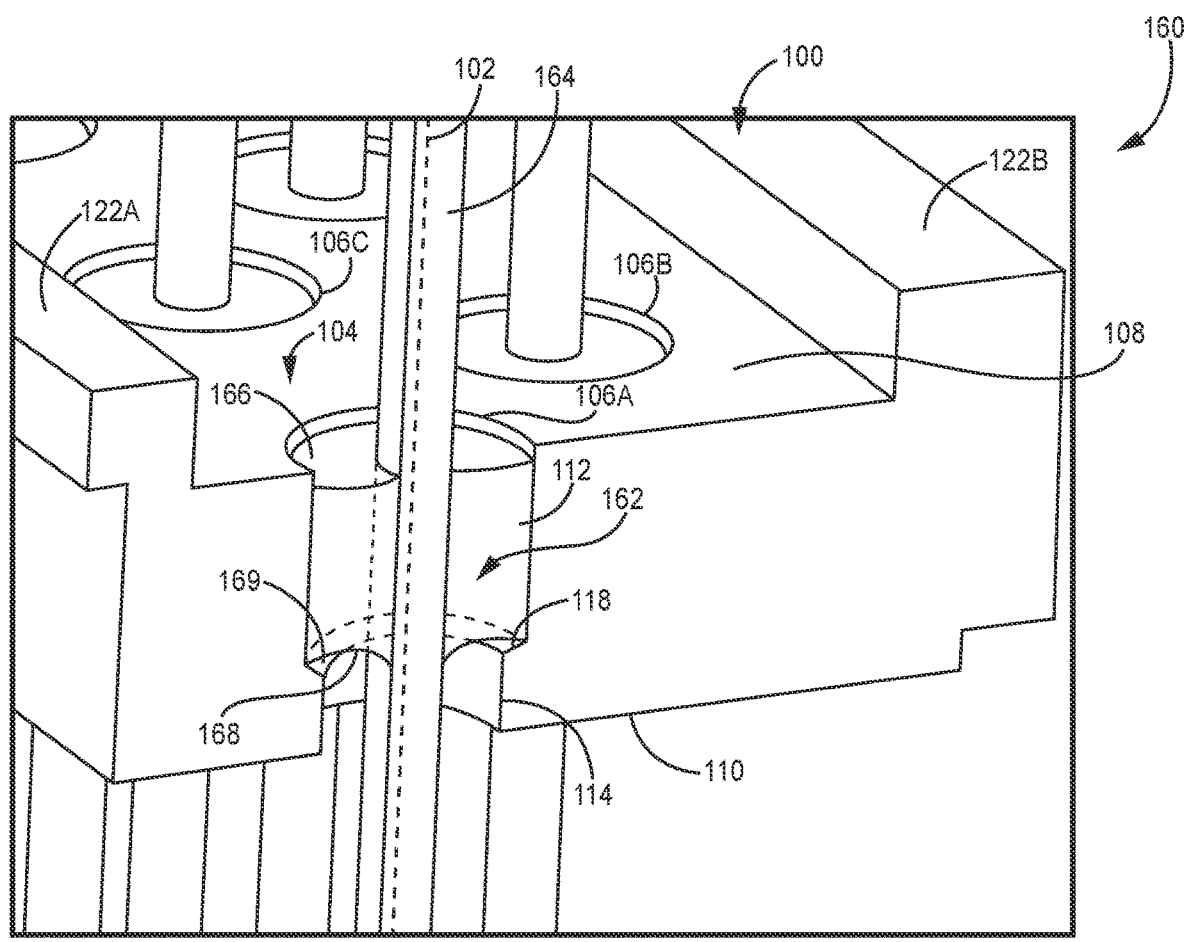
FIG. 6 is a cross-sectional view of another example feedthrough assembly that includes the header structure of FIG. 4, where the cross-section is taken through an aperture of the plurality of apertures along a plane parallel to a longitudinal axis defined by the aperture.
Figure 7:
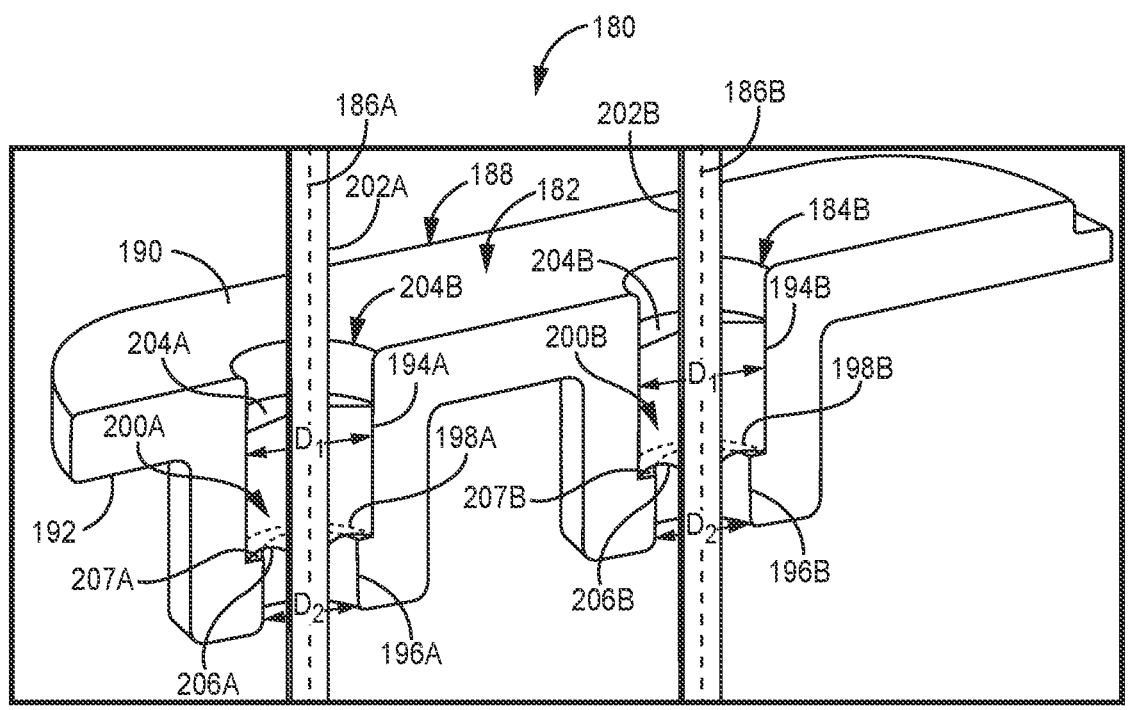
FIG. 7 is a cross-sectional view of another example feedthrough assembly that includes a ferrule defining two apertures, where the cross-section is taken through the apertures along a plane parallel to longitudinal axes defined by the apertures.
Figure 8:
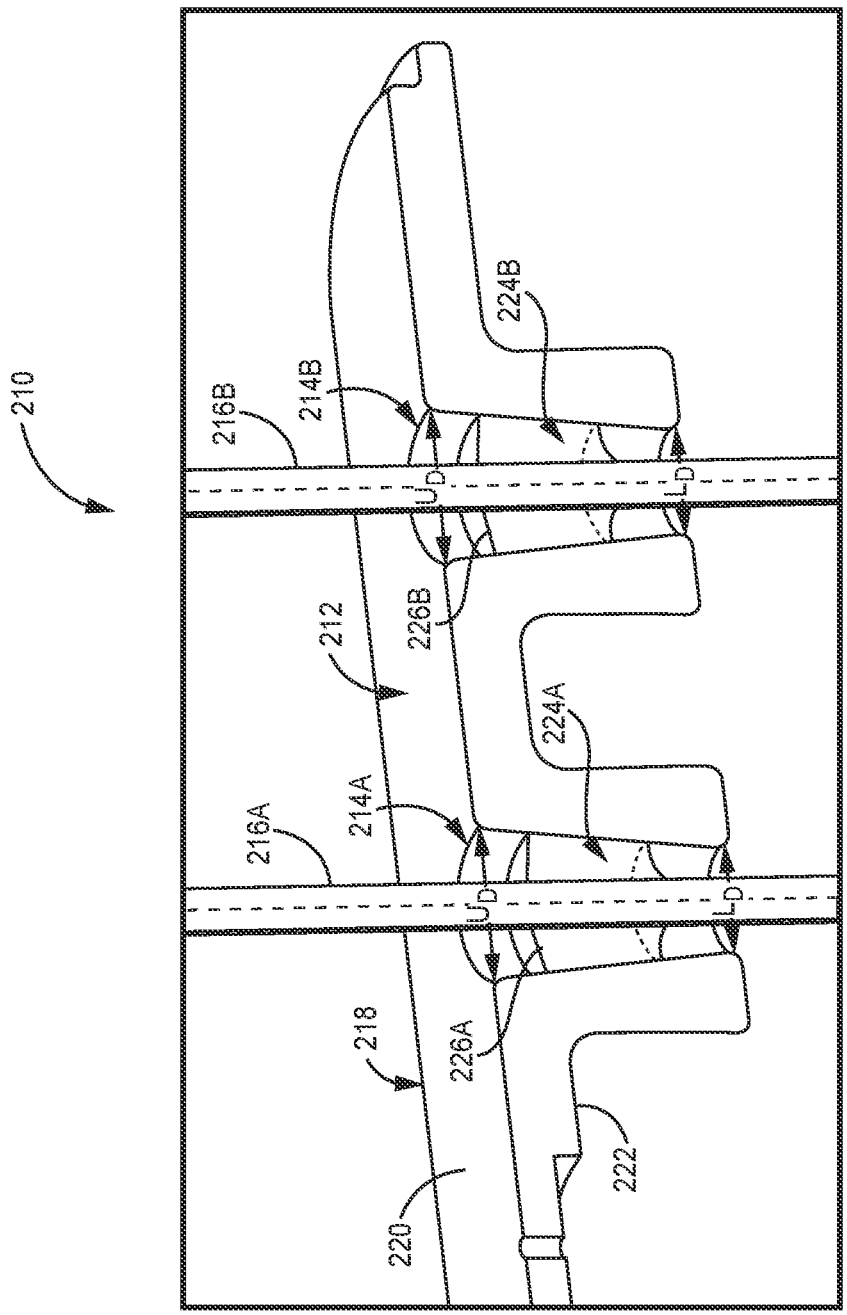
FIG. 8 is a cross-sectional view of another example feedthrough assembly that includes a ferrule that defines two apertures, where the cross-section is taken through the apertures along a plane parallel to longitudinal axes defined by the apertures.

FIGS. 4-8 are cross-sectional views of example feedthrough assemblies, and portions of example feedthrough assemblies, that are configured for attachment to suitable corresponding medical devices. FIGS. 4-7 are cross-sectional views of example feedthrough assemblies, and portions of example feedthrough assemblies, that each include a ferrule that defines at least one aperture and a ledge between first and second portions of each aperture of the at least one aperture defined by the ferrule. FIG. 8 is a cross-sectional view of an example feedthrough assembly that includes a ferrule defining two apertures that each taper in diameter from an upper diameter to a lower diameter.

Figure 4:
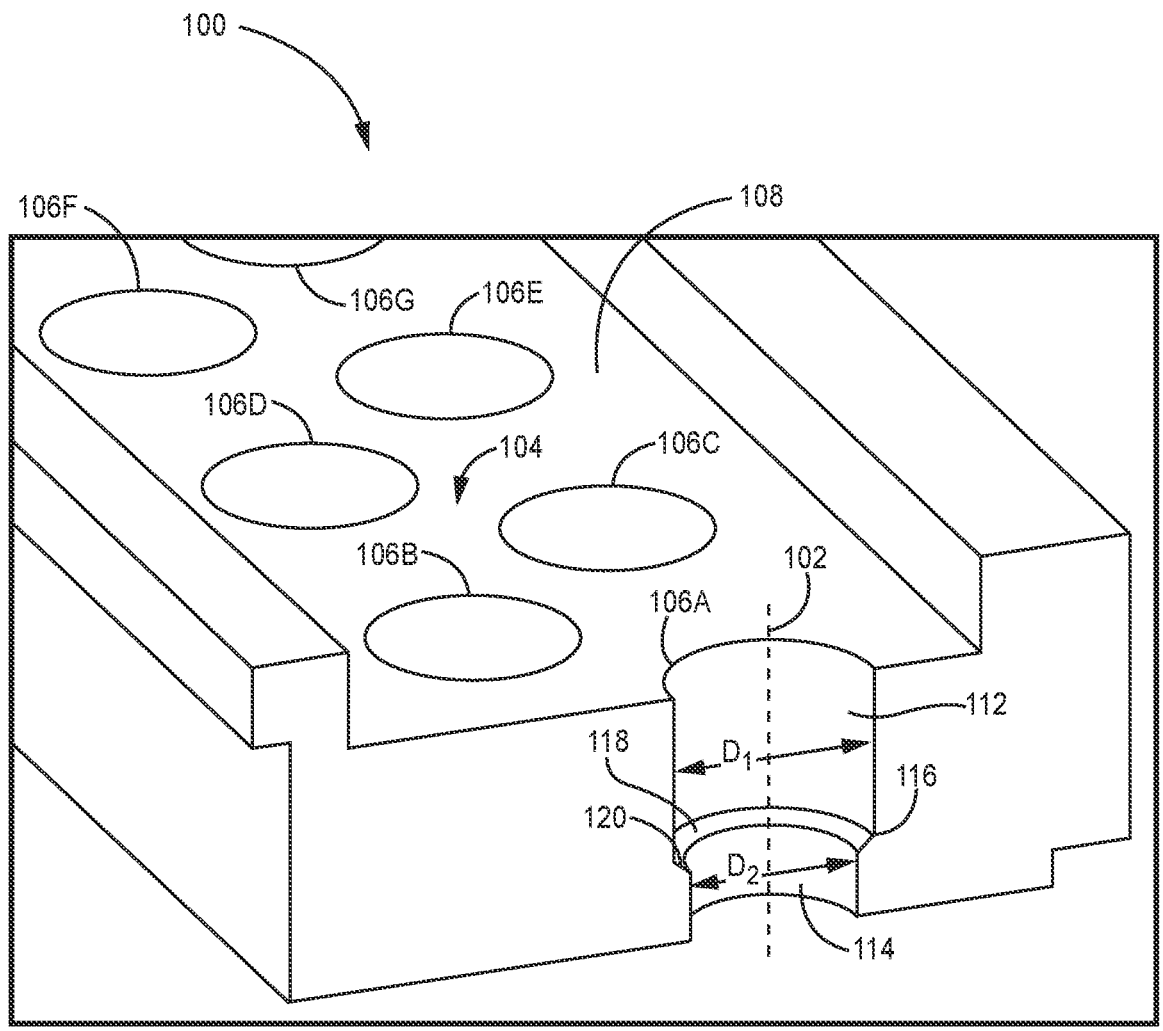
FIG. 4 is a cross-sectional view of a multi-seal header structure that may be included in an example feedthrough assembly, where the cross-section is taken along a plane parallel to a longitudinal axis of one of a plurality of apertures defined by a ferrule of the header structure and through the aperture.

FIG. 4 is a cross-sectional view of a multi-seal header structure 100 of that may be included in an example feedthrough assembly, where the cross-section is taken along a plane parallel to a longitudinal axis 102 of an aperture 106A of a plurality of apertures 106A-106G defined by a ferrule 104 of header structure 100 and through aperture 106A. In some examples, header structure 100 may be formed of titanium or another suitable metal. Header structure 100 may be 3D-printed, molded, or manufactured according to any other suitable technique.

Header structure 100 may be configured for attachment to a particular medical device, such as a medical device having one or more features of IMD 4A. For example, the plurality of apertures 106A-106G defined by ferrule 104 may enable a corresponding plurality of electrical connections between a medical device to which header structure 100 may be attached and a plurality of electrical leads. Header structure 100 is shown in FIG. 4 independently of other components of a feedthrough assembly in which header structure 100 may be included. During a method of manufacturing a feedthrough assembly that includes header structure 100, additional components may be positioned within the plurality of apertures 106A-106G defined by ferrule 104 of header structure 100, as illustrated in FIG. 6 and described below with respect to FIG. 6.

Header structure 100 defines an outer end surface 108 and an inner end surface 110 opposite outer end surface 108. A portion of outer end surface 108 may be an outer end surface defined by ferrule 104 and a portion of inner end surface 110 may be an inner end surface defined by ferrule 104. Outer end surface 108 may be more proximate to an outside of a housing of a medical device to which header structure 100 may be attached (e.g., housing 60 of IMD 4A) and inner end surface 110 may be more proximate to an inside of the housing of the medical device to which header structure 100 may be attached. Apertures 106A-106G each extend through ferrule 104 from outer end surface 108 to inner end surface 110. In some examples, apertures 106A-106G may be drilled into ferrule 104 during a method of manufacturing header structure 100.

As illustrated in FIG. 4, an aperture 106A of apertures 106A-106G includes a first portion 112 and a second portion 114. First portion 112 may extend from outer end surface 108 to a point 116 at least halfway from outer end surface 108 to inner end surface 110. Second portion 114 may extend from inner end surface 110 toward point 116. First portion 112 may have a first diameter $D_1$, which may be from about 0.02 inches to about 0.15 inches depending on the dimensions of other components of a feedthrough assembly that includes header structure 100 and the desired electrical performance of such a feedthrough assembly. Second portion 114 may have a second diameter $D_2$ that is less than $D_1$. For example, $D_1$ and $D_2$ may be selected to account for machining offsets. In some such examples, a common offset may be about ±0.002 inches for both a conductive pin and an insulating member that may be received within aperture 106A, and a gap of about 0.001 inches may be allowed for assembly. Thus, in some examples, second diameter $D_2$ may be at least about 0.005 inches less than $D_1$ to account for the common offset for the conductive pin and the insulating member and the gap allowed for assembly.

In the example of FIG. 4, first portion 112 of aperture 106A extends about two-thirds of the way between outer end surface 108 and inner end surface 110 to point 116, although this proportion may vary in other examples. In any such examples, point 116 may be located at least halfway from outer end surface 108 to the inner end surface, which may enable an insulating member to be positioned within aperture 106A such that the insulating member does not extend past outer end surface 108. Although apertures 106A-106G are illustrated in the example of FIG. 4, ferrule 104 may define additional apertures or fewer apertures in other examples. In any such examples, one or more of apertures 106A-106G may have the same or different configurations as one or more others of apertures 106A-106G. In addition, although only aperture 106A is described below in detail for the sake of clarity, a configuration of any of apertures 106B-106G may be substantially similar to the configuration of aperture 106A.

Ferrule 104 may further define a ledge 118 between first portion 112 of aperture 106A and second portion 114 of aperture 106A. Ledge 118 may extend radially inward into aperture 106A toward longitudinal axis 102 defined by ferrule 104. In the example of FIG. 4, ledge 118 defines a third portion 120 of aperture 106A that extends between first portion 112 and second portion 114. Ledge 118 may provide support for an insulating member received within aperture 106A during a method of manufacturing a feedthrough assembly that includes header structure 100 at least prior to heating and melting of the insulating member. In some examples, the support provided by ledge 118 to an insulating member may help control a position and/or shape that one or more portions of the insulating member assumes after the insulating member re-solidifies during a method of manufacturing a feedthrough assembly that includes header structure 100 (e.g., subsequent to heating and melting of the insulating member). Additionally, or alternatively, ledge 118 may define a surface onto which adhesive applied to a lower surface of an insulating member may adhere. One or more advantages that ledge 118 may provide to a feedthrough assembly that includes header structure 100 are further discussed below with respect to FIG. 6.

A diameter of third portion 120 tapers from $D_1$ at a junction of the third portion and the first portion to $D_2$ at a junction of third portion 120 and second portion 114. In some examples, a portion of ferrule 104 that defines third portion 120 of aperture 106A may form an angle with a portion of ferrule 104 that defines first portion 112 of aperture 106A that corresponds to an angle of a drill bit used to drill apertures 106A-106G, such as a standard 60° drill bit angle. In such examples, the tapered diameter of third portion 120 may correspond to a tapered dimension of a drill bit used to drill aperture 106A and facilitate machining of aperture 106A during a method of manufacturing header structure 100.

The tapered diameter of third portion 120 that corresponds to a tapered dimension of a drill bit used to drill aperture 106A may render aperture 106A easier and/or less costly to manufacture than ledges having other configurations. In some examples, drilling to form aperture 106A may include at least two steps. For example, a first drill bit having a larger diameter may be followed with a second drill bit having a smaller diameter and an angled tip. Using a second smaller diameter bit to complete aperture 106A may avoid vertical scratches in ferrule 104 that, if deep enough, may create a leak paths through the seal formed by the insulating member. However, in other examples, a ledge defined by any of the example ferrules described herein may define a surface in a plane substantially orthogonal to a longitudinal axis defined by an example ferrule, such as illustrated in FIGS. 5 and 7 and described below with respect to FIGS. 5 and 7.

In any such examples, header structure 100 may define one or more features that may be configured to facilitate attachment of header structure 100 to a medical device. For example, outer end surface 108 of header structure 100 may define ledges 122A and 122B. Ledges 122A, 122B may be configured to integrate with one or more portions of a medical device to which a feedthrough assembly that includes header structure 100 may be attached. For example, ledges 122A, 122B may be configured to integrate with a device shield such as a metal "can" of a medical device. In some examples, a metal can of such a medical device may have a thickness of about 0.01 inches to about 0.02 inches. One or more portions of such a metal can may be configured to be positioned over one or more of ledges 122A, 122B. In some examples, ledges 122A, 122B may help facilitate welding (e.g., laser welding) of header assembly 100 to a metal can of a medical device.

Figure 5:
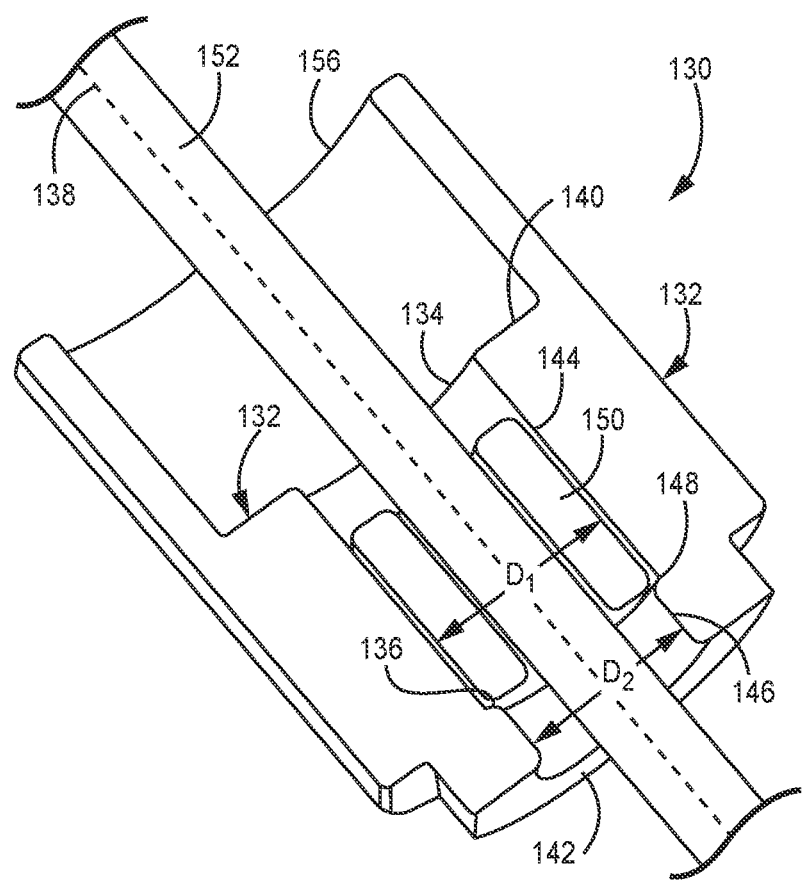
FIG. 5 is a cross-sectional view of another example feedthrough assembly that includes a ferrule defining a single aperture, where the cross-section is taken through the aperture and along a plane parallel to a longitudinal axis defined by the aperture, prior to melting an insulating member of the feedthrough assembly during a method of manufacturing the feedthrough assembly.

FIG. 5 is a cross-sectional view of another example feedthrough assembly 130 that includes a ferrule 132 that defines a single aperture 134 and a ledge 136, where the cross-section is taken through aperture 134 and along a plane parallel to a longitudinal axis 138 defined by aperture 134. FIG. 5 illustrates feedthrough assembly 130 during a method of manufacturing feedthrough assembly 130 and prior to steps of heating, melting, and re-solidifying one or more components of feedthrough assembly 130 during such a method.

Ferrule 132 may be formed of titanium or another suitable metal, such as by 3D-printing, molding, or any other suitable manufacturing technique. Ferrule 132 may be configured for attachment to a particular medical device, such as a medical device having one or more features of IMD 4B. For example, ferrule 132 may enable a corresponding electrical connection between a leadless medical device to which feedthrough assembly 130 may be attached and an electrode positioned on an exterior of the medical device, such as electrode 74 of IMD 4B. One or more features of ferrule 132 may be substantially similar to one or more corresponding features of ferrule 104 of FIG. 4. For example, ferrule 132 may define an outer end surface 140 and an inner end surface 142, and an aperture 134. Outer end surface 140 may be more proximate to an outside of a housing of a medical device to which ferrule 132 may be attached (e.g., housing 70 of IMD 4B) and inner end surface 142 may be more proximate to an inside of the housing of the medical device to which ferrule 132 may be attached. Aperture 134 may extend through ferrule 132 from outer end surface 140 to inner end surface 142, and may include a first portion 144 and a second portion 146. First portion 144 may extend from outer end surface 140 to a point 148 at least halfway from outer end surface 140 to inner end surface 142. Second portion 146 may extend from inner end surface 142 toward point 148. First portion 144 may have a first diameter $D_1$, which may be from about 0.02 inches to about 0.15 inches, depending on the dimensions of other components of feedthrough assembly 130 and the desired electrical performance of feedthrough assembly 130. Second portion 146 may have a second diameter $D_2$ that is less than $D_1$. For example, $D_1$ and $D_2$ may be selected to account for machining offsets, as discussed with respect to aperture 106A of FIG. 4, such that second diameter $D_2$ may be at least about 0.005 inches less than $D_1$ to account for the common offset for the conductive pin and the insulating member and the gap allowed for assembly.

In the example of FIG. 5, first portion 144 of aperture 134 extends about four-fifths of the way from outer end surface 140 to inner end surface 142 to point 148, although this proportion may vary in other examples. In any such examples, point 148 may be located at least halfway from outer end surface 140 to inner end surface 142, which may enable an insulating member 150 to be positioned within aperture 134 such that insulating member 150 and does not extend past outer end surface 140.

As illustrated in FIG. 5, insulating member 150 may be received within aperture 134 such that insulating member 150 surrounds at least a portion of a conductive pin 152 that also is received within aperture 134. Conductive pin 152 may be formed of a suitable conductive material, such as niobium, titanium, or alloys thereof. Conductive pin 152 may be dimensioned for use with a particular medical device. For example, conductive pin 152 may be dimensioned for use with IMD 4B. In such examples, conductive pin 152 may have a length of about 0.1 inches to about 2 inches and a width of about 0.05 inches to about 0.1 inches, although conductive pin may have any suitable dimensions for use with IMD 4B. Insulating member 150 may be dimensioned to at least partially surround conductive pin 152 when conductive pin 152 is received within aperture 134.

In some examples, insulating member 150 may be configured to electrically insulate conductive pin 152 from ferrule 132. For example, insulating member 150 may be made of an insulating material that is configured to melt and flow when heated. In some examples, insulating member 150 may be made of a glass material and may be configured to melt and flow into contact with conductive pin 152 when heated during a method of manufacturing feedthrough assembly 130. In any such examples, insulating member 150 may support conductive pin 152 within ferrule 132 at least after insulating member 150 re-solidifies.

Glass material of insulating member 150 may have any suitable composition. For example, glass material of insulating member 150 may comprise, by mole percentage, about 30% BO, about 30% to about 40% of a member selected from the group consisting of CaO, MgO, SrO and combinations thereof, where the individual amounts of CaO and MgO each do not exceed about 20%. The composition further may comprise, by mole percentage about 5% LaO, about 10%, SiO, and about 15% $Al_2O_3$. Other suitable compositions for a glass material of insulating member 150 are described in U.S. Pat. No. 8,288,654 by Taylor et al., the entire content of which is incorporated herein by reference. Such glass compositions may provide one or more benefits, such as a long-term durability and/or a reduced propensity for tensile cracks relative to other glass compositions.

In the example of FIG. 5, ledge 136 is positioned between first portion 144 of aperture 134 and second portion 146 of aperture 134 and may extend radially inward into aperture 134 toward longitudinal axis 138 defined by ferrule 132. As illustrated in FIG. 5, ledge 136 may provide support for insulating member 150 during a method of manufacturing feedthrough assembly 130 at least prior to heating and melting of the insulating member.

The support provided by ledge 136 to insulating member 150 prior to heating and melting of insulating member 150 may help control a position and/or shape that one or more portions of insulating member 150 assumes as the insulating member 150 re-solidifies during a method of manufacturing feedthrough assembly 130. For example, ledge 136 may help control the position and/or shape of an upper surface of the insulating member relative to conductive pin 152. Controlling the position and/or shape of insulating member 150 may provide one or more benefits. For example, the position of the upper surface of insulating member 150 relative to conductive pin 152 (i.e., where insulating member 150 is "pinned") affects the length of a portion of conductive pin 152 that extends above the upper surface of insulating member 150. The length of the portion of the conductive pin 152 that extends above the upper surface of insulating member 150 (i.e., the "beam length" of conductive pin 152), which may affect one or more aspects of the mechanical performance of conductive pin 152, such as the cyclic fatigue of conductive pin 152.

Additionally, or alternatively, ledge 136 may define a surface onto which adhesive applied to a surface of insulating member 150 adjacent ledge 136 may adhere. During steps of a method for manufacturing feedthrough assembly subsequent to the illustrated example of FIG. 5, insulating member 150 may be heated, then lift from ledge 136 and re-solidify to define a space between ledge 136 and a surface of insulating member 150 that is adjacent to ledge 136. As discussed below with respect to the example feedthrough assembly of FIG. 6, an adhesive coated onto the surface of an insulating member adjacent a ledge (e.g., ledge 136) may adhere to a surface of the ledge that partially defines such a space, which may create a "lock" between the adhesive and one or more insulating member 150, conductive pin 152, or ledge 136.

In some examples, ledge 136 may differ from ledge 118 in that ledge 136 may define a surface in a plane substantially orthogonal to longitudinal axis 138. As illustrated in FIG. 5, ledge 136 may further define a chamfered edge surface extending between the plane substantially orthogonal to longitudinal axis 138 that defines a third portion of aperture 134 that tapers from diameter $D_1$ of first portion 144 of aperture 134 to diameter $D_2$ of second portion 146 of aperture 134. In other examples, ledge 136 may not define a chamfered edge surface, but instead may have a configuration similar to the configuration of ledge 118 illustrated in FIG. 4.

In any such examples, ferrule 132 may further include an upper portion 156 that at least partially surrounds and extends from a perimeter of outer end surface 140 of ferrule 132. Upper portion 156 of ferrule 132 may be integral with outer end surface 140 or attached to outer end surface 140, such as via welding. Upper portion 156 may be configured to help retain a portion of a medical device to which feedthrough assembly 130 in a desired position relative to feedthrough assembly 130. For example, upper portion 156 may be configured to help retain cap 72 and/or electrode 74 of IMD 4B in a desired position relative to feedthrough assembly 130. In examples in which IMD 4B includes an electrical lead or other examples in which feedthrough assembly 130 is configured to be electrically connect an electrical lead (e.g., electrodes of an electrical lead) to a pulse generator of a medical device, upper portion 156 may be configured to help retain the lead relative to feedthrough assembly 130 In any such examples, upper portion 156 of ferrule 132 may help maintain an electrical connection between one or more electrodes of a medical device and a pulse generator of the medical device via feedthrough assembly 130.

FIG. 6 is a cross-sectional view of another example feedthrough assembly 160 that includes header structure 100 of FIG. 4, where the cross-section is taken through aperture 106A along a plane parallel to longitudinal axis 102 defined by aperture 106A. FIG. 6 illustrates the components of feedthrough assembly 160 subsequent to steps of heating, melting, and re-solidifying of a glass insulating member 162 that may be conducted during a method of manufacturing feedthrough assembly 160. Insulating member 162 may be received within aperture 106A such that insulating member surrounds at least a portion of a conductive pin 164 received within aperture 106A.

In some examples, one or more features of insulating member 162 and/or conductive pin 164 may be substantially similar to one or more corresponding features of insulating member 150 and/or conductive pin 152 of feedthrough assembly 130 of FIG. 5. For example, insulating member 162 may be a glass insulating member having a substantially similar composition to insulating member 150. However, dimensions of one or more features of insulating member 162 and/or conductive pin 164 may differ from corresponding dimensions of insulating member 150 and/or conductive pin 152. For example, insulating member 162 and/or conductive pin 164 may be dimensioned for use with IMD 4A instead of IMD 4B. In such examples, conductive pin 164 may have a length of about 0.1 inches to about 2 inches and a width of about 0.05 inches to about 0.1 inches. Insulating member 162 may be dimensioned to at least partially surround conductive pin 164 when conductive pin 164 is received within aperture 106A.

In the example of FIG. 6, insulating member 162 has been melted, flowed into contact with conductive pin 164 and allowed to re-solidify. In this manner, insulating member 162 may support conductive pin within ferrule 104 at least after insulating member 162 re-solidifies. As illustrated in FIG. 6, insulating member 162 may define an upper surface 166 and a lower surface 168. In some examples, ledge 118 may support insulating member 162 in a desired position within aperture 106A at least prior to heating of insulating member 162. One or more other factors, such as dimensions and/or composition of insulating member 162, may affect an extent to which insulating member 162 flows upon melting. Although such other factors may influence the position and/or shape that upper surface 166 and/or lower surface 168 may assume, such factors may be controllable during manufacturing of insulating member 162. However, the positioning of insulating member 162 prior to heating and melting of insulating member 162 also may influence the position and/or shape that upper surface 166 and/or lower surface 168 may assume. Thus, the support provided to insulating member 162 by ledge 118 at least prior to heating of insulating member 162 may help control the position and/or shape that upper surface 166 and/or lower surface 168 may assume as insulating member 162 re-solidifies.

In some examples, the position of upper surface 166 of insulating member 162 relative to conductive pin 164 (i.e., where insulating member 162 is "pinned") affects the length of a portion of conductive pin 152 that extends above upper surface 166 of insulating member 162. The length of the portion of the conductive pin 164 that extends above upper surface 166 (i.e., the "beam length" of conductive pin 164) may affect the mechanical performance of conductive pin 164, such as by affecting the cyclic fatigue of conductive pin 164. The influence that ledge 118 may have position and/or shape that upper surface 166 assumes as insulating member 162 re-solidifies may affect the beam length of conductive pin 164. Thus, in some examples, the support provided by ledge 118 to insulating member 162 may help ensure desirable mechanical performance of feedthrough assembly 160.

Additionally, or alternatively, ledge 118 may enable manufacturing of feedthrough assembly 160 without relying on a pedestal (e.g., a graphite pedestal) of a support platform to provide support to insulating member 162. As the use of such pedestals may be associated with breakage and/or contamination with foreign materials of one or more components of feedthrough assembly 160, manufacturing feedthrough assembly 160 without relying on such pedestals may reduce or eliminate such drawbacks. In this manner, ledge 118 may help enable consistent manufacturing of feedthrough assembly 160 to one or more desired specifications, and/or may help improve the yield of methods of manufacturing feedthrough assembly 160.

In some examples, insulating member 162 may be configured lift from ledge 118 and re-solidify during a method of manufacturing feedthrough assembly 160 to form a space 169 between ledge 118 and lower surface 168 of insulating member 168. For example, insulating member 162 may be configured to lift from ledge 118 about 0.05 millimeters (mm) to about 2.0 mm as it re-solidifies. Feedthrough assembly 160 may further include an adhesive coated onto lower surface 168 of insulating member 162 adjacent the ledge 118. In some such examples, the adhesive fills at least a portion of space 169 and adheres to ledge 118 in addition to insulating member 162 and conductive pin 164. In such examples, ledge 118 may define surface space of ferrule 104 to which adhesive may adhere in addition to a surface of ferrule 104 that defines second portion 114 of aperture 106A. Moreover, a position of the surface of ledge 118 relative to the surface of ferrule 104 that second portion 114 of aperture 106A may help create a "lock" between the adhesive and ledge 118. In this manner, ledge 118 may help improve adhesion between components of feedthrough assembly 160 and contribute to the mechanical integrity of feedthrough assembly 160.

FIG. 7 is a cross-sectional view of another example feedthrough assembly 180 that includes a ferrule 182 defining apertures 184A and 184B, where the cross-section is taken through apertures 184A and 184B along a plane parallel to longitudinal axes 186A and 186B defined by apertures 184A and 184B. Feedthrough assembly 180 may be configured for attachment to a particular medical device, such as a medical device that includes two electrical leads. For example, ferrule 182 may enable two corresponding electrical connections between a medical device to which feedthrough assembly 180 may be attached and two electrical leads via apertures 184A, 184B.

Ferrule 182 may be part of a header structure 188, which defines an outer end surface 190 and an inner end surface 192. Outer end surface 190 may be more proximate to an outside of a housing of a medical device to which header structure 188 may be attached and inner end surface 192 may be more proximate to an inside of the housing of the medical device to which header structure 188 may be attached. Portions of outer end surface 190 may be an outer end surface defined by ferrule 182 and portions of inner end surface 192 may be an inner end surface defined by ferrule 182. One or more features of feedthrough assembly 180 may be substantially similar to one or more corresponding features of feedthrough assembly 160 of FIG. 6 and thus will not be discussed in detail with respect to FIG. 7. For example, one or both of ferrule 182 may be substantially similar to ferrule 104 of feedthrough assembly 160.

Apertures 184A, 184B may be substantially similar to aperture 106A of feedthrough assembly 160. For example, apertures 184A and 184B may include first portions 194A, 194B and second portions 196A, 196B. As in aperture 106A, first portions 194A, 194B may have a first diameter and second portions 196A and 196B may have a second diameter that is greater than the first diameter.

Ferrule 182 respectively may define ledges 198A, 198B positioned between respective ones of first portions 194A, 194B and second portions 196A, 196B. Feedthrough assembly further may include insulating members 200A, 200B received within respective ones of apertures 184A, 184B. One or more features of insulating members 200A, 200B may be substantially similar to one or more corresponding features of insulating member 162 of feedthrough assembly 160. For example, insulating members 200A, 200B may be received within respective ones of apertures 184A, 184B such that insulating members 200A, 200 at least partially surround conductive pins 202A, 202B that also are received within respective ones of apertures 184A, 184B.

Feedthrough assembly 180 may differ from feedthrough assembly 160 in that ledges 198A, 198B may define respective surfaces in a plane substantially orthogonal to longitudinal axes 186A, 186B, instead of defining third portions of apertures 184A, 184B that taper in diameter from the first diameter to the second diameter.

Insulating members 200A, 200B define upper surfaces 204A, 204B and lower surfaces 206A, 206B. In some examples, the positions and/or shapes of upper surfaces 204A, 204B may be substantially similar to the position and/or shape of upper surface 166 of insulating member 162 of feedthrough assembly 160. The positions and/or shapes of lower surfaces 206A, 206B may be substantially similar to the position and/or shape of lower surface 168 of insulating member 162. For example, lower surfaces 206A, 206B respectively may define spaces 207A and 207B between ledges 198A, 198B and respective lower surfaces 206A, 206B during a method of manufacturing feedthrough assembly 160 (e.g., after the temperature of insulating members 200A, 200B falls to a point where the insulting members no longer flow. Spaces 207A, 207B may be differently sized and/or shaped than space 169 defined between lower surface 168 of insulating member 162 and ledge 118 due to the different configurations of ledges 198A, 198B relative to ledge 118. Nonetheless, spaces 207A, 207B defined between lower surfaces 206A, 206B and ledges 198A, 198B may provide one or more advantages similar to those described above with respect to space 169 defined between lower surface 168 of insulating member 162 and ledge 118 of feedthrough assembly 160.

FIG. 8 is a cross-sectional view of another example feedthrough assembly 210 that includes a ferrule 212 that defines two apertures 214A and 214B, where the cross-section is taken through apertures 214A and 214B along a plane parallel to longitudinal axes 216A and 216B defined by apertures 214A, 214B. Feedthrough assembly 210 may be substantially similar to feedthrough assembly 180 illustrated in FIG. 7. Thus, features of feedthrough assembly 210 that corresponding to one or more features of feedthrough assembly 180 will not be discussed in detail with respect to FIG. 8. For example, feedthrough assembly 210 may include a header structure 218 that includes ferrule 212 and defines an outer end surface 220 and an inner end surface 222. Outer end surface 220 may be more proximate to an outside of a housing of a medical device to which header structure 218 may be attached and inner end surface 222 may be more proximate to an inside of the housing of the medical device to which header structure 218 may be attached. Header structure 218 may be substantially similar to header structure 188 of feedthrough assembly 180.

Feedthrough assembly 210 may differ from feedthrough assembly 180 in that the configurations of apertures 214A, 214B differ from the configurations of apertures 184A, 184B. For example, instead of including a first portion having a first diameter and a second portion having a second diameter that is less than the first diameter, diameters of apertures 184A, 184B may taper from an upper diameter $U_D$ near outer end surface 218 to an inner diameter $I_D$ near inner end surface 220. In some examples, the taper between $U_D$ and $I_D$ may be substantially continuous, as illustrated in FIG. 8. In any such examples, ferrule 212 may not define a ledges between first and second portions of apertures 214A, 214B. Instead, the tapered diameters of apertures 214A, 214B may provide one or more of the advantages described above with respect to example ferrules that define a ledge.

For example, the tapered diameters of apertures 214A, 214B also may help retain insulating members 224A and 224B in a desired position within apertures 214A, 214B at least prior to heating insulating members 224A, 224B. In such examples, the insulating members 224A, 224B may have a substantially continuous diameter prior to heating, similar to insulating member 150 of feedthrough assembly 130 of FIG. 5. The diameter of insulating members 224A, 224B prior to heating may be smaller than $U_D$ and greater than $I_D$. Thus, when insulating members 224A, 224B are received within respective ones of apertures 214A, 214B prior to heating, insulating members 224A, 224B may be supported within apertures 214A, 214B in a position where the diameter of apertures 214A, 214B is substantially similar to the diameter of insulating members 224A, 224B. The support provided to insulating members 224A, 224B by the tapered diameters of apertures 214A, 214B at least prior to heating of insulating members 224A, 224B also may help position (e.g., relative to respective ones of conductive pins 228A, 228B) and/or shape that upper surfaces 226A and 226B may assume as insulating members 224A, 224B flow and then re-solidify during a method of manufacturing feedthrough assembly 210.

Additionally, or alternatively, the tapered diameter of apertures 214A, 214B may enable manufacturing of feedthrough assembly 210 without relying on pedestals (e.g., graphite pedestals) of a support platform to provide support to insulating members 224A, 224B. Thus, the tapered diameters of apertures 214A, 214B may reduce or eliminate drawbacks associated with such graphite pedestals as described above with respect to the example feedthrough assemblies of FIGS. 5-7.

Figure 9:
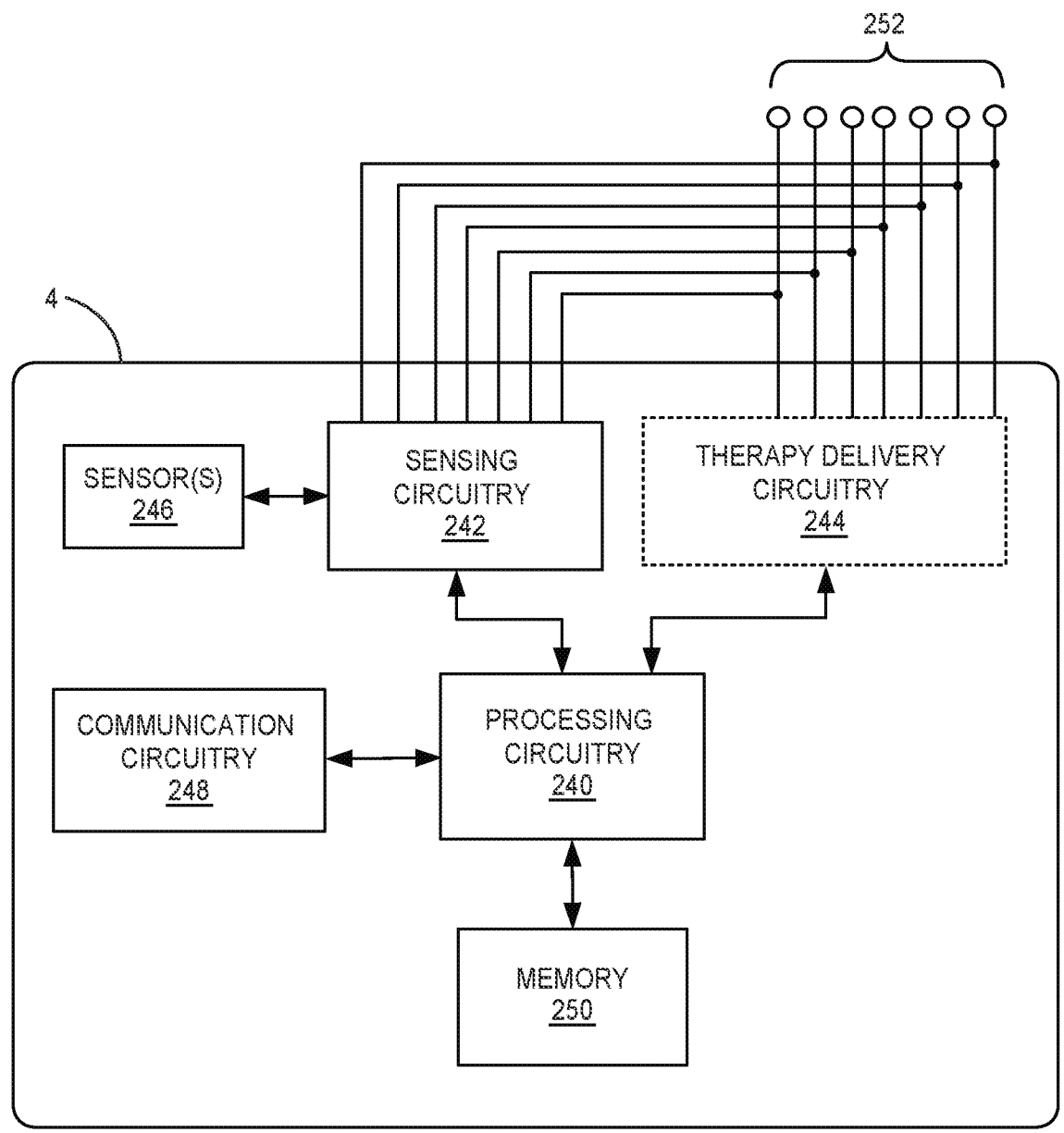
FIG. 9 is a functional block diagram illustrating an example configuration of the implantable medical device of FIG. 2.

FIG. 9 is a functional block diagram illustrating an example configuration of an IMD 4A. In some examples, one or more components of IMD 4 may be substantially similar to one or more corresponding components of any of IMD 4A of FIG. 1 or IMD 4B of FIG. 2. As shown in FIG. 9, IMD 4 includes processing circuitry 240, sensing circuitry 242, therapy delivery circuitry 244, sensors 246, communication circuitry 248, and memory 250. In addition, IMD 4 includes one or more electrodes 252, which may be any one or more electrodes of IMD 4A or one or more electrodes of IMD 4B. In some examples, memory 250 includes computer-readable instructions that, when executed by processing circuitry 240, cause IMD 4 and processing circuitry 240 to perform various functions attributed to IMD 4 and processing circuitry 240 herein. Memory 250 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 240 may include fixed function circuitry and/or programmable processing circuitry. Processing circuitry 240 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 240 may include multiple components, such as any combination of one or more microprocessors, one or more controllers, one or more DSPs, one or more ASICs, or one or more FPGAs, as well as other discrete or integrated logic circuitry. The functions attributed to processing circuitry 240 herein may be embodied as software, firmware, hardware or any combination thereof.

In some examples, processing circuitry 240 may receive (e.g., from external device 18), via communication circuitry 248, a respective value for each of a plurality of cardiac sensing parameters, cardiac therapy parameters (e.g., cardiac pacing parameters), and/or electrode vectors. Processing circuitry 240 may store such parameters and/or electrode vectors in memory 250.

Therapy delivery circuitry 244 and sensing circuitry 242 are electrically coupled to electrodes 252, which may include one or more of electrodes 252. Processing circuitry 240 is configured to control therapy delivery circuitry 244 to generate and deliver electrical stimulation to heart 6 via electrodes 252. Electrical stimulation may include, for example, pacing pulses, or any other suitable electrical stimulation. Processing circuitry 240 may control therapy delivery circuitry 244 to deliver electrical stimulation therapy via electrodes 252 according to one or more therapy programs including pacing instructions that define a pacing rate, which may be stored in memory 250.

In addition, processing circuitry 240 is configured to control sensing circuitry 242 to monitor signals from electrodes 252 in order to monitor electrical activity of a patient's heart. Sensing circuitry 242 may include circuits that acquire electrical signals. Sensing circuitry 242 may acquire electrical signals from a subset of electrodes 252. Electrical signals acquired by sensing circuitry 242 may include intrinsic and/or paced cardiac electrical activity, such as atrial depolarization and/or ventricular depolarization. Sensing circuitry 242 may filter, amplify, and digitize the acquired electrical signals to generate raw digital data. Processing circuitry 240 may receive the digitized data generated by sensing circuitry 242. In some examples, processing circuitry 240 may perform various digital signal processing operations on the raw data, such as digital filtering.

In some examples, in addition to sensing circuitry 242, IMD 4 optionally may include sensors 246, which may comprise at least one of a variety of different sensors. For example, sensors 246 may comprise one or more pressure sensors and/or one or more accelerometers. Sensors 246 may detect signals associated with one or more physiological parameters of a patient, such as an activity level, a hemodynamic pressure, and/or heart sounds. Processing circuitry 240 may use signal detected by sensors 246 to adapt one or more cardiac pacing parameters, such as by increasing a rate of delivery of pacing pulses in response to detecting an increase in the patient's activity level.

Communication circuitry 248 may include any suitable hardware (e.g., an antenna), firmware, software, or any combination thereof for communicating with another device, such as an external device (e.g., a device configured for use in a home, ambulatory, clinic, or hospital setting to communicate with IMD 4 via wireless telemetry) or a patient monitor. Under the control of processing circuitry 240, communication circuitry 248 may receive downlink telemetry from and send uplink telemetry to other devices (e.g., external device 18) such as via an antenna included in communication circuitry 248.

Figure 10:
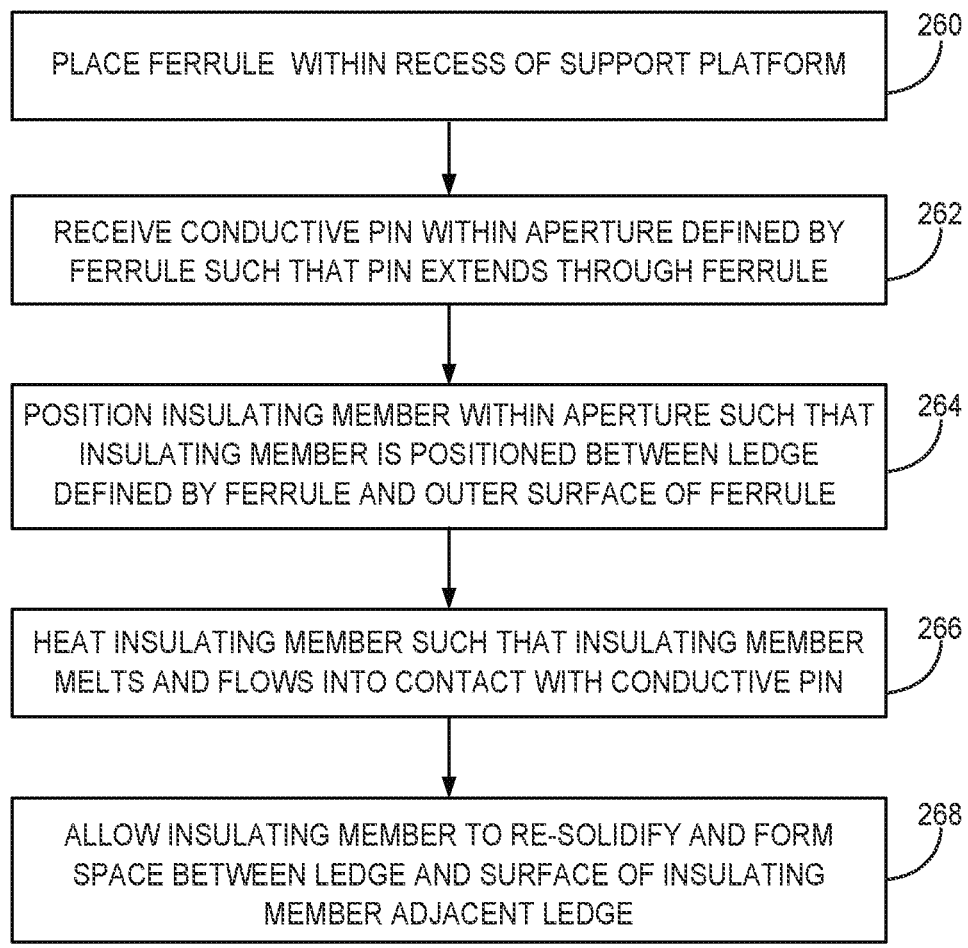
FIG. 10 is a flow diagram illustrating an example technique for manufacturing a feedthrough assembly.

FIG. 10 is a flow diagram illustrating an example technique for manufacturing a feedthrough assembly for a medical device. Although the example technique of FIG. 10 is described in the context of feedthrough assembly 160 of FIG. 6, the example technique should not be understood to be so limited, but instead may be applied to the manufacture of other example feedthrough assemblies within the scope of this disclosure.

The example technique of FIG. 10 includes receiving at least a portion of ferrule 104 within a recess defined by a support platform and dimensioned to receive at least the portion of ferrule 104 (260). For example, at least a portion of inner end surface 192 defined by ferrule 104 may be received within the recess. In some examples, the support platform may be substantially similar to support platform 92 of FIG. 3 and the recess may be substantially similar to a recess of recesses 94 defined by support platform 92. Conductive pin 164 may be received within aperture 106A defined by ferrule 104 (262). For example, conductive pin 164 may be received within aperture 106A such that conductive pin 164 extends through ferrule 104. In some such examples, conductive pin 164 may be positioned such that a portion of conductive pin 164 that extends from inner end surface 110 is supported by a surface of support platform 92 that defines a bottom interior portion of the recess of recesses 94. Receiving conductive pin 164 within aperture 106A such that the portion of conductive pin 164 is supported by support platform 92 may help retain conductive pin 164 in a desired position relative to ferrule 104 during the example technique of FIG. 10.

Insulating member 162 may be received within aperture 106A and around conductive pin 164 such that at least a portion of insulating member 162 is positioned between ledge 118 defined by ferrule 104 and a portion of outer end surface 108 defined by ferrule 104 (264). For example, insulating member 162 may be received within aperture 106A such that insulating member 162 is supported by ledge 118 within aperture 106A. With conductive pin 164 and insulating member 162 so positioned, insulating member 162 may be heated such that insulating member 162 melts and flows into contact with conductive pin 164 (266). As discussed with respect to FIG. 6, insulating member 162 may be a glass insulating member. Thus, heating insulating member 162 may include heating insulating member 162 to a temperature sufficient to cause melting of glass having the composition and configuration of insulating member 162.

After insulating member 162 melts and flows into contact with conductive pin 164 during heating of insulating member 162, the application of heat to insulating member 162 may be reduced or discontinued and insulating member 162 may be allowed to re-solidify. In some examples, insulating member 162 may be configured to support conductive pin 164 within ferrule 104 at least after insulating member 162 re-solidifies. Insulating member 162 may lift from ledge 118 when above a flow temperature (e.g., due to surface tension of insulating member 162 causing insulating member 162 to contract and lift) and re-solidify, such that ledge 118 and lower surface 168 of insulating member define a space therebetween (268). For example, insulating member 162 may be lifted from ledge 118 by about 0.05 mm to about 2.0 mm as insulating member 162 re-solidifies. In some examples, the space may help reduce a possibility of residual stress between ledge 118 and insulating member 162. Moreover, as described below, the space defined by ledge 118 and lower surface 168 of insulating member 162 may enable better adhesion between an adhesive applied to lower surface 168 of insulating member 162 and conductive pin 164 relative to other example feedthrough assemblies in which such a space is not defined.

In some examples, a method of manufacturing feedthrough assembly 160 may further include removing feedthrough assembly 160 from support platform 92 after allowing insulating member 162 to re-solidify. After removing feedthrough assembly 160 from support platform 92, ferrule 104 may be attached to a medical device (e.g., IMD 4A of FIG. 1), such that a first portion of conductive pin 164 extends from inner end surface 110 into housing 60 of IMD 4A and a second portion of conductive pin 164 extends from outer end surface 108 outside of housing 60.

In some examples, after feedthrough assembly 160 is removed from support platform 92, a method of manufacturing feedthrough assembly 160 may further include applying an adhesive to lower surface 168 of insulating member 162 adjacent ledge 118 such that the adhesive fills at least a portion of the space defined by ledge 118 and lower surface 168 of insulating member 162. In such examples, the adhesive may be in contact with conductive pin 164 along a length of conductive pin 164 that is adjacent the portion of the space filled by the adhesive. Filling at least a portion of the space defined by ledge 118 and lower surface 168 of insulating member 162 with the adhesive may help secure the position of conductive pin 164 relative to one or more other components of feedthrough assembly 160 (e.g., insulating member 162 and/or ferrule 104). Securing the position of conductive pin 164 relative to such other components of feedthrough assembly 160 in such a manner may provide one or more advantages, such as contributing to the mechanical integrity of feedthrough assembly 160 and/or the integrity of the electrical coupling of the components of feedthrough assembly 160 to other components of a medical device to which feedthrough assembly may be attached.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:
1. A method of manufacturing a feedthrough assembly for a medical device, the method comprising:
receiving at least a portion of a ferrule configured for attachment to the medical device within a recess defined by a support platform and dimensioned to receive at least the portion of the ferrule, the ferrule defining:
an outer end surface and an inner end surface;
an aperture extending through the ferrule from the outer end surface to the inner end surface, the aperture comprising:
a first portion extending from the outer end surface to a point at least halfway from the outer end surface to the inner end surface, the first portion having a first diameter; and
a second portion extending from the inner end surface toward the point at least halfway from the outer end surface to the inner end surface, the second portion having a second diameter that is less than the first diameter,
wherein the aperture defines a longitudinal axis extending through the aperture from the outer end surface to the inner end surface; and
a ledge between the first portion of the aperture and the second portion of the aperture, the ledge extending radially inward toward the longitudinal axis, wherein the ledge defines a third portion of the aperture extending between the first portion and the second portion, and wherein a diameter of the third portion tapers from the first diameter at a junction of the third portion and the first portion to the second diameter at a junction of the third portion and the second portion
receiving a conductive pin within the aperture such that the conductive pin extends through the ferrule;
receiving an insulating member configured to electrically insulate the conductive pin from the ferrule within the aperture and around at least a portion of the conductive pin such that at least a portion of the insulating member is positioned between the ledge and the outer end surface of the ferrule;
heating the insulating member such that the insulating member melts and flows into contact with the conductive pin; and
discontinuing heating of the insulating member and allowing the insulating member to re-solidify,
wherein the insulating member is configured lift from the ledge such that the ledge and a surface of the insulating member adjacent the ledge define a space therebetween.

2. The method of claim 1, wherein the insulating member is supported by the ledge within the aperture at least prior to heating of the insulating member.

3. The method of claim 1, wherein the insulating member is configured to support the conductive pin within the ferrule at least after the insulating member re-solidifies.

4. The method of claim 1, wherein the aperture comprises a plurality of apertures, the feedthrough assembly, and wherein the feedthrough assembly further comprises a header structure configured for attachment to the medical device and comprising the ferrule.

5. The method of claim 1, wherein the insulating member comprises a glass insulating member.

6. The method of claim 1, further comprising applying adhesive to the surface of the glass insulating member adjacent the ledge such that the adhesive fills at least a portion of the space.

7. The method of claim 1, wherein receiving at least the portion of the ferrule within the recess comprises receiving at least the inner end surface of the ferrule within the recess.

8. The method of claim 1, wherein the ledge defines a surface in a plane substantially orthogonal to the longitudinal axis.

9. The method of claim 8, further comprising:
removing the feedthrough assembly from the support platform after allowing the insulating member to re-solidify; and
attaching the ferrule to the medical device such that a first portion of the conductive pin extends from the inner end surface into a housing of the medical device and a second portion of the conductive pin extends from the outer end surface outside of the housing.

* * * * *